(12) United States Patent
Zillmann et al.

(10) Patent No.: US 12,350,340 B2
(45) Date of Patent: *Jul. 8, 2025

(54) VISCOSITY REDUCTION OF HIGHLY CONCENTRATED PROTEIN FORMULATIONS

(71) Applicant: Merck Patent GmbH, Darmstadt (DE)

(72) Inventors: Martin Zillmann, Shrewsbury, MA (US); Alexandra Krog, Bodenheim (DE); Raphael Guebeli, Darmstadt (DE); Tanja Henzler, Mannheim (DE); Christian Hildebrandt, Heppenheim (DE)

(73) Assignee: Merck Patent GmbH, Darmstadt (DE)

( * ) Notice: Subject to any disclaimer, the term of this patent is extended or adjusted under 35 U.S.C. 154(b) by 374 days.

This patent is subject to a terminal disclaimer.

(21) Appl. No.: 17/542,632

(22) Filed: Dec. 6, 2021

(65) Prior Publication Data

US 2022/0088200 A1 Mar. 24, 2022

Related U.S. Application Data

(62) Division of application No. 16/385,715, filed on Apr. 16, 2019, now Pat. No. 11,207,412.

(60) Provisional application No. 62/666,311, filed on May 3, 2018.

(30) Foreign Application Priority Data

Apr. 16, 2018 (EP) .................................... 18167609

(51) Int. Cl.
| | | |
|---|---|---|
| A61K 39/395 | (2006.01) | |
| A61K 9/00 | (2006.01) | |
| A61K 9/19 | (2006.01) | |
| A61K 47/18 | (2017.01) | |
| A61K 47/20 | (2006.01) | |
| A61K 47/26 | (2006.01) | |

(52) U.S. Cl.
CPC ............ *A61K 47/26* (2013.01); *A61K 9/0095* (2013.01); *A61K 9/19* (2013.01); *A61K 47/183* (2013.01); *A61K 47/20* (2013.01)

(58) Field of Classification Search
None
See application file for complete search history.

(56) References Cited

U.S. PATENT DOCUMENTS

| | | |
|---|---|---|
| 4,816,567 A | 3/1989 | Cabilly et al. |
| 5,641,870 A | 6/1997 | Rinderknecht et al. |
| 8,703,126 B2 | 4/2014 | Liu et al. |
| 8,900,525 B2 | 12/2014 | Ponaka et al. |
| 9,023,790 B2 | 5/2015 | Heimbecher et al. |
| 9,320,797 B2 | 4/2016 | Sloey et al. |
| 9,358,297 B2 | 6/2016 | Heimbecher et al. |
| 10,179,172 B2 | 1/2019 | Larson et al. |
| 10,478,498 B2 | 11/2019 | Soane et al. |
| 11,207,412 B2 * | 12/2021 | Zillmann ................ A61K 9/08 |
| 11,660,343 B2 | 5/2023 | Soane et al. |
| 11,696,951 B2 | 7/2023 | Wuthrich et al. |
| 2002/0045571 A1 | 4/2002 | Liu et al. |
| 2009/0117097 A1 | 5/2009 | Igawa |
| 2010/0297106 A1 | 11/2010 | Sloey et al. |
| 2013/0058958 A1 | 3/2013 | Bowen et al. |
| 2017/0232103 A1 | 8/2017 | Soane et al. |
| 2018/0289804 A1 | 10/2018 | Blake-Haskins et al. |

FOREIGN PATENT DOCUMENTS

| | | |
|---|---|---|
| CN | 102958528 A | 3/2013 |
| CN | 106535918 A | 3/2017 |
| JP | 2004532798 A | 10/2004 |
| JP | 2010503410 A | 2/2010 |
| JP | 2012-206977 A | 10/2012 |
| JP | 2013525484 A | 6/2013 |
| JP | 2016534141 A | 11/2016 |
| JP | 2017-515909 A | 6/2017 |
| JP | 2017519018 A | 7/2017 |
| WO | 09043049 A2 | 4/2009 |
| WO | 11139718 A1 | 11/2011 |

OTHER PUBLICATIONS

Du et al: "Hydrophobic salts markedly diminish viscosity of concentrated protein solutions", Biotechnology and Bioengineering, vol. 108, No. 3, 2010, pp. 632-636.

Guo et al: ‚Structure—Activity Relationship for hydrophobic salts as viscosity-lowering excipients for concentrated solutions of monoclonal antibodies, Pharm. Research, vol. 29, No. 11, pp. 3182-3189, 2012.

Koehler et al: 'Continuous cultures of fused cells secreting antibody of predefined specificity', Nature; vol. 256, pp. 495-497, 1975.

Clackson et al: 'Making antibody fragment using phage display libraries', Nature, vol. 352, pp. 624-628, 1991.

Marks et al: 'By-passing Immunization Human antibodies from V-gene libraries displayed on phage', J. Mol. Bioi., vol. 222, p. 581-597,1991.

Morrison et al: 'Chimeric antibody molecules: Mouse antigen-binding domains with human constant region domains', Proc. Natl. Acad. Sci. USA, vol. 81, pp. 6851-6855;1984.

Zapata et al: 'Engineering linear F(ab')2 fragments for efficient production in *Escherichia coli* and enhanced antiproliferative activity', Prot. Eng., vol. 8, Issue 10, pp. 1057-1062, 1995.

Jones et al: 'Replacing the complementarity-determining regions in a human antibody with those from a mouse', Nature; vol. 321; pp. 522-525, 1986.

Riechmann et al: 'Rechaping human antibodies for therapy', Nature, vol. 332, pp. 323-327; 1988.

Presta et al: 'Antibody Engineering', Curr. Op. Struct. Bioi., vol. 3, Issue 4, pp. 394-398, 1992.

(Continued)

*Primary Examiner* — Yunsoo Kim

(74) *Attorney, Agent, or Firm* — Millen, White, Zelano & Branigan, P.C.; Brion P. Heaney

(57) ABSTRACT

The present invention relates to compositions of highly concentrated protein formulations showing reduced viscosity. The contained proteins in the prepared formulations are stabilized against aggregation and denaturation and are thus sufficiently storage-stable until administration to the patient.

17 Claims, 10 Drawing Sheets

(56) References Cited

OTHER PUBLICATIONS

Figure 1:
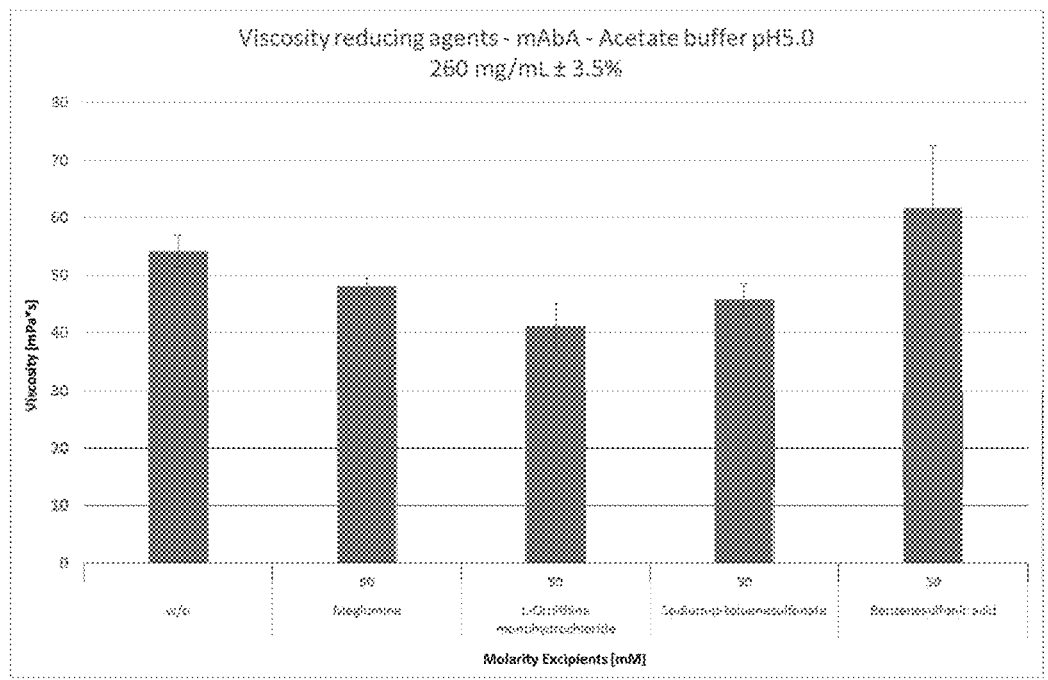

Wei Du, Alexander M. Klibanov; "Hydrophobic salts markedly diminish viscosity of concentrated protein solutions" Biotechnology and Bioengineering, 2010, vol. 108, No. 3, p. 632-636 ; https://doi.org/10.1002/bit.22983.
Office Action in corresponding JP Appln.2020-556852 dispatched Feb. 24, 2023 (pp. 1-2).
English translation of Office Action in corresponding CN application 201980026524.9 dated Jun. 16, 2023 (pp. 1-18).

* cited by examiner

VISCOSITY REDUCTION OF HIGHLY CONCENTRATED PROTEIN FORMULATIONS

The present invention relates to compositions of highly concentrated protein formulations showing reduced viscosity. The contained proteins in the prepared formulations are stabilized against aggregation and denaturation and are thus sufficiently storage-stable until administration to the patient.

STATE OF THE ART

Most biotherapeutic proteinic products in development are monoclonal antibodies (mAb) or related formats such as bi-specific antibodies or antibody fragments. The therapeutic doses of such products across a broad range of clinically important indications are often high.

But peptides and proteins are larger and more complex than traditional organic and inorganic drugs (i.e. possessing multiple functional groups in addition to complex three-dimensional structures), the formulation of such proteins poses special problems. One of these problems is the increased viscosity of protein formulations, especially at high concentration.

The latter, however, is a particular problem because it is highly desirable from a patient convenience, compliance and overall healthcare cost perspective for the resultant products to be delivered via a low volume subcutaneous injection.

But a combination of the high therapeutic dose and the highly desirable low injection volume often leads to a need for very highly concentrated formulations of the active ingredient. It is well known that achieving stable aqueous formulations of biotherapeutics at high concentration can be exceptionally challenging, often leading to a considerable increase in the rate of aggregation, particle formation and in viscosity. High viscosity is unacceptable as it significantly limits the injectability of the product.

Antibody and other protein therapeutics may be administered parenterally, such as by intravenous (IV), intramuscular (IM) or subcutaneous (SC) route. Subcutaneous injection has gained increasing attention for the delivery of protein therapeutics due to its potential to simplify patient administration (fast, low-volume injection) and reduced treatment costs (shorter medical assistance). To ensure patient compliance, it is desirable that subcutaneous injection dosage forms be isotonic and include small injection volumes (<2.0 ml per injection site). To reduce injection volume, proteins are often administered within the range of 1 mg/ml to 150 mg/ml.

Thus, primarily development of protein formulations for subcutaneous administration is often associated with viscosity challenges. Volume limitations (<2 ml) and dose requirements (usually >100 mg administration) often demand for highly concentrated protein formulations. But at high concentrations, as already said, proteins tend to form highly viscous solutions and the stability can become problematic due to the formation of soluble and insoluble protein-protein aggregates. As such viscosity is a severe challenge for
a) the manufacturing process and
b) the administration to the patient.

In the manufacturing process, highly concentrated protein formulations that are highly viscous, present difficulties in processing, particularly in ultrafiltration and sterile filtration.

mAb-based therapies are usually administered repeatedly over an extended period of time and require several mg/kg dosing. Antibody solutions or suspensions can be administered via parenteral routes, such as by intravenous (IV) infusions, and subcutaneous (SC) or intramuscular (IM) injections. Here, in injection solutions, the high viscosity is a problem. To solve this problem and to improve the stability of the solution, additives and excipients in higher concentrations are usually added as well. At protein concentrations that are desirable for formulations intended for intramuscular or subcutaneous administration, high concentrations of stabilizers, such as sucrose and sodium chloride, are required to achieve long-term protein stability. The resulting solutions often cause injection pain due high injection forces and to tissue damages. Therefore, it is critical to balance the needed amounts of stabilizers for stability and osmolarity of the high protein concentration formulations.

As a consequence, the technical hurdles attributed to viscosity oftentimes lead to failure to develop protein formulations for subcutaneous delivery.

In order to increase success rates in the development of subcutaneous formulations, the reduction of and control of viscosity by chemical ways has gained considerable attention in recent years.

A large number of publications and patent applications refer to excipients from the family of salts (mostly NaCl) and of special amino acids, preferably arginine, histidine and proline, which have shown to be efficient in lowering the viscosity of certain high-concentration protein therapeutics.

Unfortunately, these well-known approaches for lowering the viscosity are not universally applicable, probably due to the fact that the viscosity of protein formulations is the result of various intermolecular forces. Depending on the protein molecule and its formulation conditions, different interactions may affect the viscosity, such as molecular crowding, or dipole interactions or interactions between hydrophobic or charged groups. Consequently, the pharmaceutical industry has a strong need for viscosity-reducing excipients, especially as an alternative option when standard solutions based on NaCl and amino acids mentioned above, fail.

A high number of viscosity lowering additives and excipients has been researched in the past. Nowadays, one of the most prominent ones is arginine, besides histidine, lysine, and camphor-10-sulfonic acid. In a research paper from Zheng Guo et al., ("Structure-Activity Relationship for Hydrophobic Salts as Viscosity-Lowering Excipients for Concentrated Solutions of Monoclonal Antibodies", Pharmaceutical Research, vol. 29, no. 11, Jun. 13, 2012, p. 3182-3189) many more unique molecules are described exhibiting viscosity lowering properties. At present, still not all therapeutic proteins solutions exhibiting viscosity issues at high concentration can be adequately addressed by the known viscosity-lowering excipients.

OBJECT OF THE PRESENT INVENTION

Protein formulations (e.g. monoclonal antibodies, fusion proteins etc.) intended for pharmaceutical applications usually require stabilizers against undesired aggregation and to prevent physical or chemical degradation. These problems are worsened at high protein concentrations which are often desirable for therapeutic administration of this class of molecules.

At high concentrations, the proteins tend to self-associate, resulting in high viscosity formulations, and complicating e.g. the administration of these protein solutions by injection, but also of manufacturing processes, in which a tangential flow filtration is often used for the buffer exchange and for the increase of protein concentration. By increasing the back pressure and shear stress during injection and filtration, the therapeutic protein is potentially destabilized or process times are prolonged. Accordingly, there is a high need within the biopharmaceutical industry for formulation additives and excipients, or combinations thereof, with viscosity lowering features. However, formulating proteins like monoclonal antibodies requires a careful selection of formulation additives and/or excipients to avoid protein denaturation and/or loss of biological activity.

But still a high number of emerging new antibodies and antibody-formats require the development of suitable, innovative viscosity lowering additives and/or excipients or of specific additive/excipient combinations or of targeted formulation strategies. These additives/excipients have to be pharmaceutically safe because protein formulations are administered parenterally, which includes the intravenous, intramuscular, intraperitoneal, intradermal or subcutaneous route. Accordingly, the additives which can be used in these formulations must be physiologically compatible and must not have any undesired side effects and must under no circumstances lead to allergic reactions; in particular, they must not cause any anaphylactoid side effects.

SUBJECT-MATTER OF THE INVENTION

The subject of the present invention is a method for reducing the viscosity of a liquid highly concentrated formulation of a pharmaceutically active protein comprising the step of combining the protein solution with a viscosity-reducing concentration of an excipient selected from the group consisting of meglumine, ornithine, carnitine, benzenesulfonic acid and sodium p-toluene sulfonic acid, gluconic acid, glucuronic acid, aminocaproic acid and succinate or mixtures thereof. In particular, the present invention relates to formulations in which the concentration of the protein is in the range of at least 50 mg/ml up to 300 mg/ml and wherein the therapeutic protein is selected from the group of antibodies, antibody fragments, minibody, a modified antibody, antibody-like molecule and fusion protein.

Particularly good viscosity-lowering effects are achieved by the claimed methods when meglumine is added together with benzenesulfonic acid as counterion or sodium p-toluene sulfonic acid as counterion, but also if ornithine and benzenesulfonic acid as counterions are added or ornithine or sodium p-toluene sulfonic as counterion, or of further suitable combinations, which are effective. This effect is achieved in particular when these combinations are added in equimolar amounts. Especially by adding said excipients mentioned, a reduction of the viscosity of at least 12% can be achieved and under optimum conditions of up to 80%.

A concentrated pharmaceutical formulation of a pharmaceutically active protein or peptide including the claimed embodiments is also an object of the present invention. The therapeutic protein may be selected from the group of antibodies, antibody fragments, minibody, a modified antibody, antibody-like molecule and fusion proteins. Furthermore, the method, such as claimed, for producing lyophilized powders from compositions such as claimed is an object of this invention. Additionally, kits containing the claimed compositions is also within the scope of this invention.

DETAILED DESCRIPTION OF THE INVENTION

As outlined above, high protein concentrations pose challenges relating to the physical and chemical stability of the protein, as well as difficulties with manufacture, storage, and administration of the protein formulation. A major problem is the tendency of proteins to aggregate and form particulates during processing and/or storage, which makes manipulations during further processing and/or administration difficult. Concentration-dependent degradation and/or aggregation are major challenges in developing protein formulations at higher concentrations. In addition to the potential for non-native protein aggregation and particulate formation, reversible self-association in aqueous solutions may occur, which contributes to, among other things, increased viscosity that complicates delivery by injection.

Definitions

The term "protein," as generally used herein, refers to a polymer of amino acids linked to each other by peptide bonds to form a polypeptide for which the chain length is sufficient to produce at least a detectable tertiary structure. Proteins having a molecular weight (expressed in kDa wherein "Da" stands for "Daltons" and 1 kDa=1,000 Da) greater than about 100 kDa may be designated "high-molecular-weight proteins," whereas proteins having a molecular weight less than about 100 kDa may be designated "low-molecular-weight proteins." The term "low-molecular-weight protein" excludes small peptides lacking the requisite of at least tertiary structure necessary to be considered a protein. Protein molecular weight may be determined using standard methods known to one skilled in the art, including, but not limited to, mass spectrometry (e.g., ESI, MALDI) or calculation from known amino acid sequences and glycosylation. Proteins can be naturally occurring or non-naturally occurring, synthetic, or semi-synthetic.

"Essentially pure protein(s)" and "substantially pure protein(s)" are used interchangeably herein and refer to a composition comprising at least about 90% by weight pure protein, preferably at least about 95% pure protein by weight. "Essentially homogeneous" and "substantially homogeneous" are used interchangeably herein and refer to a composition wherein at least about 90% by weight of the protein present is a combination of the monomer and reversible di- and oligomeric associates (not irreversible aggregates), preferably at least about 95%.

The term "antibody," as generally used herein, broadly covers mAbs (including full-length antibodies which have an immunoglobulin Fc region), antibody compositions with polyepitopic specificity, bispecific antibodies, diabodies, and single-chain antibody molecules, as well as antibody fragments (e.g., Fab, Fab', F(ab')2, and Fv), single domain antibodies, multivalent single domain antibodies, Fab fusion proteins, and fusions thereof.

The term "monoclonal antibody" or "mAb," as generally used herein, refers to an antibody obtained from a population of substantially homogeneous antibodies, i.e., the individual antibodies comprising the population are identical, except for possible naturally occurring mutations that may be present in minor amounts. Monoclonal antibodies are highly specific, being directed against a single epitope. These are typically synthesized by culturing hybridoma cells, as described by Kohler et al. (*Nature* 256: 495, 1975), or may be made by recombinant DNA methods (see, e.g., U.S. Pat. No. 4,816,567), or isolated from phage antibody libraries using the techniques described in Clackson et al. (*Nature* 352: 624-628, 1991) and Marks et al. (*J. Mol. Biol.* 222: 581-597, 1991), for example. As used herein, "mAbs" specifically include derivatized antibodies, antibody-drug conjugates, and "chimeric" antibodies in which a portion of the heavy and/or light chain is identical with or homologous to corresponding sequences in antibodies derived from a particular species or belonging to a particular antibody class or subclass, while the remainder of the chain(s) is (are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA* 81:6851-6855, 1984).

An "antibody fragment" comprises a portion of an intact antibody, including the antigen binding and/or the variable region of the intact antibody.

Examples of antibody fragments include Fab, Fab', F(ab')2, and Fv fragments; diabodies; linear antibodies (see U.S. Pat. No. 5,641,870; Zapata et al., *Protein Eng.* 8:1057-1062, 1995); single-chain antibody molecules; multivalent single domain antibodies; and multispecific antibodies formed from antibody fragments.

"Humanized" forms of non-human (e.g., murine) antibodies are chimeric immunoglobulins, immunoglobulin chains, or fragments thereof (such as Fv, Fab, Fab', F(ab')2, or other antigen-binding subsequences of antibodies) of mostly human sequences, which contain minimal sequences derived from non-human immunoglobulin. (See, e.g., Jones et al., *Nature* 321:522-525, 1986; Reichmann et al., *Nature* 332:323-329, 1988; and Presta, *Curr. Op. Struct. Biol.* 2:593-596, 1992.)

In this context, the term "therapeutically active protein" is understood to mean, in simple terms, that it is a protein or peptide which is selected from the group of antibodies, antibody fragments, minibody, a modified antibody, antibody-like molecule and fusion protein and which is defined as described above.

"Rheology" refers to the study of the deformation and flow of matter and "viscosity" refers to the resistance of a substance (typically a liquid) to flow. Viscosity is related to the concept of shear force; it can be understood as the effect of different layers of the fluid exerting shearing force on each other, or on other surfaces, as they move against each other. There are several measures of viscosity. The units of viscosity are $Ns/m^2$, known as Pascal-seconds (Pa-s). Viscosity can be "kinematic" or "absolute". Kinematic viscosity is a measure of the rate at which momentum is transferred through a fluid. It is measured in Stokes (St). The kinematic viscosity is a measure of the resistive flow of a fluid under the influence of gravity. When two fluids of equal volume and differing viscosity are placed in identical capillary viscometers and allowed to flow by gravity, the more viscous fluid takes longer than the less viscous fluid to flow through the capillary. If, for example, one fluid takes 200 seconds (s) to complete its flow and another fluid takes 400 s, the second fluid is called twice as viscous as the first on a kinematic viscosity scale. The dimension of kinematic viscosity is length$^2$/time. Commonly, kinematic viscosity is expressed in centiStokes (cSt). The SI unit of kinematic viscosity is $mm^2/s$, which is equal to 1 cSt. The "absolute viscosity," sometimes called "dynamic viscosity" or "simple viscosity," is the product of kinematic viscosity and fluid density. Absolute viscosity is expressed in units of centipoise (cP). The SI unit of absolute viscosity is the milliPascal-second (mPa-s), where 1 cP=1 mPa-s.

Viscosity may be measured by using, for example, a viscometer at a given shear rate or multiple shear rates. An "extrapolated zero-shear" viscosity can be determined by creating a best fit line of the four highest-shear points on a plot of absolute viscosity versus shear rate, and linearly extrapolating viscosity back to zero-shear. Alternatively, for a Newtonian fluid, viscosity can be determined by averaging viscosity values at multiple shear rates. Viscosity can also be measured using a microfluidic viscometer at single or multiple shear rates (also called flow rates), wherein absolute viscosity is derived from a change in pressure as a liquid flows through a channel. Viscosity equals shear stress over shear rate. Viscosities measured with microfluidic viscometers can, in some embodiments, be directly compared to extrapolated zero-shear viscosities, for example those extrapolated from viscosities measured at multiple shear rates using a cone and plate viscometer.

"Shear rate" refers to the rate of change of velocity at which one layer of fluid passes over an adjacent layer. The velocity gradient is the rate of change of velocity with distance from the plates. This simple case shows the uniform velocity gradient with shear rate $(v_1-v_2)/h$ in units of (cm/sec)/(cm)=1/sec. Hence, shear rate units are reciprocal seconds or, in general, reciprocal time. For a microfluidic viscometer, change in pressure and flow rate are related to shear rate. "Shear rate" is to the speed with which a material is deformed. Formulations containing proteins and viscosity-lowering agents are typically measured at shear rates ranging from about 0.5 $s^{-1}$ to about 200 $s^{-1}$ when measured using a cone and plate viscometer and a spindle appropriately chosen by one skilled in the art to accurately measure viscosities in the viscosity range of the sample of interest (i.e., a sample of 20 cP is most accurately measured on a CPE40 spindle affixed to a DV2T viscometer (Brookfield)); greater than about 20 $s^{-1}$ to about 3,000 $s^{-1}$ when measured using a microfluidic viscometer.

For classical "Newtonian" fluids, as generally used herein, viscosity is essentially independent of shear rate. For "non-Newtonian fluids," however, viscosity either decreases or increases with increasing shear rate, e.g., the fluids are "shear thinning" or "shear thickening", respectively. In the case of concentrated (i.e., high-concentration) protein solutions, this may manifest as pseudoplastic shear-thinning behavior, i.e., a decrease in viscosity with shear rate.

The term "chemical stability," as generally used herein, refers to the ability of the protein components in a formulation to resist degradation via chemical pathways, such as oxidation, deamidation, or hydrolysis. A protein formulation is typically considered chemically stable if less than about 5% of the components are degraded after 24 months at 4° C.

The term "physical stability," as generally used herein, refers to the ability of a protein formulation to resist physical deterioration, such as aggregation. A formulation that is physically stable forms only an acceptable percentage of irreversible aggregates (e.g., dimers, trimers, or other aggregates) of the bioactive protein agent. The presence of aggregates may be assessed in several ways, including by measuring the average particle size of the proteins in the formulation by means of dynamic light scattering. A formulation is considered physically stable if less than about 5% irreversible aggregates are formed after 24 months at 4° C. Acceptable levels of aggregated contaminants ideally would be less than about 2%. Levels as low as about 0.2% are achievable, although approximately 1% is more typical.

The term "stable formulation," as generally used herein, means that a formulation is both chemically stable and physically stable. A stable formulation may be one in which more than about 95% of the bioactive protein molecules retain bioactivity in a formulation after 24 months of storage at 4° C., or equivalent solution conditions at an elevated temperature, such as one month storage at 40° C. Various analytical techniques for measuring protein stability are available in the art and are reviewed, for example, in Peptide and Protein Drug Delivery, 247-301, Vincent Lee, Ed., Marcel Dekker, Inc., New York, N.Y. (1991) and Jones, A.,

*Adv. Drug Delivery Revs.* 10:29-90, 1993. Stability can be measured at a selected temperature for a certain time period. For rapid screening, for example, the formulation may be kept at 40° C., for 2 weeks to one month, at which time residual biological activity is measured and compared to the initial condition to assess stability. When the formulation is to be stored at 2° C.-8° C., generally the formulation should be stable at 30° C. or 40° C. for at least one month and/or stable at 2° C.-8° C. for at least 2 years. When the formulation is to be stored at room temperature, about 25° C., generally the formulation should be stable for at least 2 years at about 25° C. and/or stable at 40° C. for at least about 6 months. The extent of aggregation following lyophilization and storage can be used as an indicator of protein stability. In some embodiments, the stability is assessed by measuring the particle size of the proteins in the formulation. In some embodiments, stability may be assessed by measuring the activity of a formulation using standard biological activity or binding assays well within the abilities of one ordinarily skilled in the art.

The term protein "particle size," as generally used herein, means the average diameter of the predominant population of bioactive molecule particulates, or particle size distributions thereof, in a formulation as determined by using well known particle sizing instruments, for example, dynamic light scattering, SEC (size exclusion chromatography), or other methods known to one ordinarily skilled in the art.

The term "concentrated" or "high-concentration", as generally used herein, describes liquid protein formulations having a final concentration of protein of at least 1 mg/ml, especially greater than about 10 mg/mL, preferably greater than about 50 mg/mL, more preferably greater than about 100 mg/mL, still more preferably greater than about 200 mg/mL, or most preferably greater than about 250 mg/mL.

A "reconstituted formulation," as generally used herein, refers to a formulation which has been prepared by dissolving a dry powder, lyophilized, spray-dried or solvent-precipitated protein in a diluent, such that the protein is dissolved or dispersed in aqueous solution for administration.

A "lyoprotectant" is a substance which, when combined with a protein, significantly reduces chemical and/or physical instability of the protein upon lyophilization and/or subsequent storage. The lyoprotectant is generally added to the pre-lyophilized formulation in a "lyoprotecting amount." This means that, following lyophilization of the protein in the presence of the lyoprotecting amount of the lyoprotectant, the protein essentially retains its physical and chemical stability and integrity.

A "diluent" or "carrier," as generally used herein, is a pharmaceutically acceptable (i.e., safe and non-toxic for administration to a human or another mammal) and useful ingredient for the preparation of a liquid formulation, such as an aqueous formulation reconstituted after lyophilization. Exemplary diluents include sterile water, bacteriostatic water for injection (BWFI), a pH buffered solution (e.g., phosphate-buffered saline), sterile saline solution, Ringer's solution or dextrose solution, and combinations thereof.

A "preservative" is a compound which can be added to the formulations herein to reduce contamination by and/or action of bacteria, fungi, or another infectious agent. The addition of a preservative may, for example, facilitate the production of a multi-use (multiple-dose) formulation.

A "bulking agent," as generally used herein, is a compound which adds mass to a lyophilized mixture and contributes to the physical structure of the lyophilized cake (e.g. facilitates the production of an essentially uniform lyophilized cake which maintains an open pore structure).

A "therapeutically effective amount" is the least concentration required to effect a measurable improvement or prevention of any symptom or a particular condition or disorder, to effect a measurable enhancement of life expectancy, or to generally improve patient quality of life. The therapeutically effective amount is dependent upon the specific biologically active molecule and the specific condition or disorder to be treated.

Therapeutically effective amounts of many proteins, such as the mAbs described herein, are well known in the art. The therapeutically effective amounts of proteins not yet established or for treating specific disorders with known proteins, such as mAbs, to be clinically applied to treat additional disorders may be determined by standard techniques which are well within the craft of a skilled artisan, such as a physician.

The term "injectability" or "syringeability," as generally used herein, refers to the injection performance of a pharmaceutical formulation through a syringe equipped with an 18-32-gauge needle, optionally thin walled. Injectability depends upon factors such as pressure or force required for injection, evenness of flow, aspiration qualities, and freedom from clogging. Injectability of the liquid pharmaceutical formulations may be assessed by comparing the injection force of a reduced-viscosity formulation to a standard formulation without added viscosity-lowering agents. The reduction in the injection force of the formulation containing a viscosity-lowering agent reflects improved injectability of that formulation. The reduced viscosity formulations have improved injectability when the injection force is reduced by at least 10%, preferably by at least 30%, more preferably by at least 50%, and most preferably by at least 75% when compared to a standard formulation having the same concentration of protein under otherwise the same conditions, except for replacement of the viscosity-lowering agent with an appropriate buffer of about the same concentration. Alternatively, injectability of the liquid pharmaceutical formulations may be assessed by comparing the time required to inject the same volume, such as 0.5 mL, or more preferably about 1 mL, of different liquid protein formulations when the syringe is depressed with the same force.

The term "injection force," as generally used herein, refers to the force required to push a given liquid formulation through a given syringe equipped with a given needle gauge at a given injection speed. The injection force is typically reported in Newtons. For example, the injection force may be measured as the force required to push a liquid formulation through a 1 mL plastic syringe having a 0.25 inch inside diameter, equipped with a 0.50-inch 27-gauge needle at a 250 mm/min injection speed. Testing equipment can be used to measure the injection force. When measured under the same conditions, a formulation with lower viscosity will generally require an overall lower injection force.

The term "reduced-viscosity formulation," as generally used herein, refers to a liquid formulation having a high concentration of a high-molecular-weight protein, such as a mAb, or a low-molecular-weight protein that is modified by the presence of one or more additives to lower the viscosity, as compared to a corresponding formulation that does not contain the viscosity-lowering additive(s) or agent(s).

The term "viscosity-lowering agent," as used herein, refers to a compound which acts to reduce the viscosity of a solution relative to the viscosity of the solution absent the viscosity-lowering agent. The viscosity-lowering agent may be a single compound or may be a mixture of one or more compounds. When the viscosity-lowering agent is a mixture of two or more compounds, the listed concentration refers to each individual agent, unless otherwise specified. By way of example, a formulation containing about 0.25 M meglumine benzenesulfonate as the viscosity-lowering agent is a solution having benzenesulfonic acid at a concentration of 0.25 M, and meglumine at a concentration of 0.25 M.

Certain viscosity-lowering agents contain acidic or basic functional groups and may show hydrophilic and hydrophobic regions, which together influence the interaction characteristics with comprising proteins of the solution. Whether or not the functional groups are fully or partially ionized depends on the pH of the formulation they are in. Unless otherwise specified, reference to a formulation containing a viscosity-lowering agent having an ionizable functional group includes both the parent compound and any possible ionized states.

The term "liquid formulation," as used herein, is a protein that is either supplied in an acceptable pharmaceutical diluent or one that is reconstituted in an acceptable pharmaceutical diluent prior to administration to the patient.

Biosimilars can be produced by microbial cells (prokaryotic, eukaryotic), cell lines of human or animal origin (e.g., mammalian, avian, insect), or tissues derived from animals or plants. The expression construct for a proposed biosimilar product will generally encode the same primary amino acid sequence as its reference product. Minor modifications, such as N- or C-terminal truncations that will not have an effect on safety, purity, or potency, may be present.

A biosimilar mAb is similar to the reference mAb physiochemically or biologically both in terms of safety and efficacy. The biosimilar mAb can be evaluated against a reference mAb using one or more in vitro studies including assays detailing binding to target antigen(s); binding to isoforms of the Fc gamma receptors (FcγRI, FcγRII, and FcγRIII), FcRn, and complement (C1q); Fab-associated functions (e.g. neutralization of a soluble ligand, receptor activation or blockade); or Fc-associated functions (e.g. antibody-dependent cell-mediated cytotoxicity, complement-dependent cytotoxicity, complement activation). In vitro comparisons may be combined with in vivo data demonstrating similarity of pharmacokinetics, pharmacodynamics, and/or safety. Clinical evaluations of a biosimilar mAb against a reference mAb can include comparisons of pharmacokinetic properties (e.g. $AUC_{0\text{-}inf}$, $AUC_{0\text{-}t}$, $C_{max}$, $t_{max}$, $C_{trough}$); pharmacodynamic endpoints; or similarity of clinical efficacy (e.g. using randomized, parallel group comparative clinical trials). The quality comparison between a biosimilar mAb and a reference mAb can be evaluated using established procedures, including those described in the "Guideline on similar biological medicinal products containing biotechnology-derived proteins as active substance: Quality issues" (EMEA/CHMP/BWP/49348/2005), and the "Guideline on development, production, characterization and specifications for monoclonal antibodies and related substances" (EMEA/CHMP/BWP/157653/2007).

Differences between a biosimilar mAb and a reference mAb can include post-translational modification, e.g. by attaching to the mAb other biochemical groups such as a phosphate, various lipids and carbohydrates; by proteolytic cleavage following translation; by changing the chemical nature of an amino acid (e.g., formylation); or by many other mechanisms.

Other post-translational modifications can be a consequence of manufacturing process operations—for example, glycation may occur with exposure of the product to reducing sugars. In other cases, storage conditions may be permissive for certain degradation pathways such as oxidation, deamidation, or aggregation, as all these product-related variants may be included in a biosimilar mAb.

As used herein, the term "pharmaceutically acceptable salts" refers to salts prepared from pharmaceutically acceptable non-toxic acids and bases, including inorganic acids and bases, and organic acids and bases.

As used herein, term "alkyl group" refers to straight-chain, branched-chain and cyclic hydrocarbon groups. Unless specified otherwise, the term alkyl group embraces hydrocarbon groups containing one or more double or triple bonds. An alkyl group containing at least one ring system is a "cycloalkyl" group. An alkyl group containing at least one double bond is an "alkenyl group," and an alkyl group containing at least one triple bond is an "alkynyl group."

The term as used herein, "Aryl" refers to aromatic carbon ring systems, including fused ring systems. In an "aryl" group, each of the atoms that form the ring are carbon atoms.

As used herein "Heteroaryl" refers to aromatic ring systems, including fused ring systems, wherein at least one of the atoms that forms the ring is a heteroatom. Furthermore, the term as used herein "Heterocycle" refers to ring systems that, including fused ring systems, are not aromatic, wherein at least one of the atoms that forms the ring is a heteroatom.

The term as used herein, "heteroatom" is any non-carbon or non-hydrogen atom. Preferred heteroatoms include oxygen, sulfur, and nitrogen.

Formulations

Biocompatible, low-viscosity protein solutions, such as those of mAbs, can be used to deliver therapeutically effective amounts of proteins in volumes useful for subcutaneous (SC) and intramuscular (IM) injections, typically less than or about 2 ml for SC and less than or about 5 ml for IM, more preferably less than or about 1 ml for SC and less than or about 3 ml for IM. The proteins can generally have any molecular weight, although in some embodiments high-molecular-weight proteins are preferred. In other embodiments the proteins are low-molecular-weight proteins.

Now, the present invention provides a method of reducing the viscosity of and/or improving stability of a liquid pharmaceutical formulation of a therapeutic protein, by combining the therapeutic protein and a viscosity-reducing amount of an excipient selected from the group consisting of meglumine, ornithine, carnitine, benzenesulfonic acid and sodium p-toluene sulfonic acid, gluconic acid, glucuronic acid, aminocaproic acid and succinate or mixtures thereof in equimolar amounts to the protein solutions. Depending on the pH value of the solution, the concentration of the protein solution, the nature of the protein, the resulting concentration of the added excipient(s) and its (their) chemical nature the viscosity reducing effect varies.

In particular, when mixtures of meglumine and ornithine together with one of the counterions selected from toluene sulfonate and benzenesulfonic acid are added in equimolar amounts to the concentrated protein solution, for example to solutions of (mAbA and mAbB), a particularly good viscosity reduction is achieved.

Unexpectedly, it was found by experiments that mixtures of the cationic amino-sugar meglumine in combination with the amino acid ornithine and a negatively charged counter ion, selected from sodium-p-toluene sulfonate and benzenesulfonic acid, as specific equimolar mixtures significantly reduce the viscosity of highly concentrated protein liquid formulations of monoclonal antibodies or of fusion proteins.

In exemplary embodiments, the therapeutic protein is at a high protein concentration as described above. In some embodiments, the reduction in viscosity is at least about 5%, 10%, 15%, 20%, 25%, 30%, 35%, 40%, 45%, 50%, 55%, 60%, 65% or 70% compared to control formulations in which buffer solution was added to the protein solution in the same amount instead of the viscosity reducing agent solution.

In exemplary embodiments, the therapeutic protein is at a high protein concentration as described above of at least 50 mg/ml, preferably more than 75 mg/ml, more preferable more than 100 mg/ml. Formulations tested and disclosed here have protein concentrations in the range of 150-280 mg/ml. In some embodiments, the reduction in viscosity is at least about 5%, 10%, 15%, 20%, 25%, 30%, 35%, 40%, 45%, 50%, 55%, 60%, 65%, 70% or 75% compared to control formulations or more.

In another aspect, the invention provides liquid solutions comprising a therapeutic protein and an excipient selected from the group consisting of meglumine, ornithine, sodium-p-toluene sulfonate, and benzenesulfonic acid or mixtures thereof wherein the formulations exhibit reduced viscosity relative to control formulations. In exemplary embodiments, the therapeutic protein is at a high protein concentration as described above, and the excipient(s) described herein is present at a viscosity-reducing (weight: volume) concentration. Any of these excipients can be used at concentrations up to their solubility limit. Such solutions may further comprise other additives in an amount effective to further improve stability, reduce aggregation, and/or make the formulation isotonic, without significantly increasing viscosity.

In further embodiments, the concentration of the excipient selected from the group consisting meglumine, ornithine, carnitine, benzenesulfonic acid and sodium p-toluene sulfonic acid, gluconic acid, glucuronic acid, aminocaproic acid and succinate or mixtures thereof is at least about 50 mM to about 300 mM, or at least about 100 mM to about 250 mM, or at least about 140 mM to about 200 mM. In exemplary embodiments the concentration of the excipient is at least about 50, 100, 105, 110, 115, 120, 125, 130, 135, 140, 145, 150, 155, 160, 165, 170, 175, 180, 185, 190, 195, 200, 210, 220, 250, or 300 mM or greater. Other exemplary embodiments include concentrations of excipients effective to make the formulation isotonic, without significantly increasing viscosity. Exemplary concentrations include those at least about 150 mM or greater, in further embodiments the amounts are at least about 170 mM or greater.

In another aspect, the invention provides lyophilized protein formulations comprising a therapeutic protein and an excipient selected from the group consisting of meglumine, ornithine, carnitine, benzenesulfonic acid and sodium p-toluene sulfonic acid, gluconic acid, glucuronic acid, aminocaproic acid and succinate or mixtures thereof wherein upon reconstitution with the recommended amount of diluent, the formulations exhibit reduced viscosity relative to control formulations. In exemplary embodiments, the therapeutic protein is at a high protein concentration as described above. In some embodiments, the excipient is present at an amount effective to reduce viscosity upon reconstitution with diluent (weight: weight concentration). Such formulations may further comprise further additives, in an amount effective to further improve stability, reduce aggregation, and/or make the formulation isotonic, without significantly increasing viscosity.

In exemplary embodiments, the concentration of the excipient selected from the group consisting meglumine, ornithine, carnitine, benzenesulfonic acid and sodium p-toluene sulfonic acid, gluconic acid, glucuronic acid, aminocaproic acid and succinate or mixtures thereof is at least about 1 µg per mg therapeutic protein, up to about 1.0 mg per mg therapeutic protein. In some embodiments, the concentration of excipient is at least about 1, 10, 50, 100, 150, 200, 250, 300, 350, 400, 450, 500 or 550 µg per mg therapeutic protein. In other exemplary embodiments, the concentration of excipient is up to about 600, 650, 700, 750, 800, 850, 900, 950 or 1000 µg per mg therapeutic protein.

In yet another embodiment, the present invention provides a method of preventing self-association of proteins in liquid formulations by using meglumine, ornithine, carnitine, benzenesulfonic acid and sodium p-toluene sulfonic acid, gluconic acid, glucuronic acid, aminocaproic acid and succinate or mixtures thereof as an excipient in any of the amounts or concentrations described herein. Formulations with improved stability (e.g., reduced aggregation) and shelf-life are also provided.

The invention also provides a kit comprising a liquid protein formulation of the invention, and instructions for its administration, optionally with a container, syringe and/or other administration device. The invention further provides a kit comprising a lyophilized protein formulation of the invention, optionally in a container, and instructions for its reconstitution and administration, optionally with a vial of sterile diluent, and optionally with a syringe or other administration device. Exemplary containers include vials, tubes, bottles, single or multi-chambered pre-filled syringes, or cartridges, but also a 96-well plate comprising ready-to-use freeze-dried or spray-dried formulations sitting in the wells. Exemplary administration devices include syringes, with or without needles, infusion pumps, jet injectors, pen devices, transdermal injectors, or other needle-free injectors.

Another aspect of the present invention is to provide a method for screening for a viscosity-reducing concentration of an excipient comprising the steps of: (1) assessing the viscosity of a first solution comprising a first concentration of an excipient selected from the group consisting of meglumine, ornithine, sodium-p-toluene sulfonate, benzenesulfonic acid, gluconic acid, glucuronic acid, aminocaproic acid, carnitine, and succinate or mixtures thereof and a therapeutic protein, such as an antibody, (2) assessing the viscosity of a second solution comprising a different second concentration of the excipient and the therapeutic protein, and (3) determining that the first concentration of excipient is more viscosity-reducing than the second concentration of excipient if the first solution is less viscous. Viscosity can be determined, e.g., using a m-VROC™ Technology rheometer (RheoSense, San Ramon, California, USA) or an Aries ARG2 Rheometer or a Brookfield RV-DVIII Rheometer.

Similar methods are provided for screening for an aggregation-reducing or stabilizing concentration of an excipient.

Stability can be assessed in many ways, including monitoring conformational change over a range of temperatures (thermostability) and/or time periods (shelf-life) and/or after exposure to stressful handling situations (e.g. physical shaking). Stability of formulations containing varying concentrations of formulation components can be measured using a variety of methods. For example, the amount of protein aggregation can be measured by visual observation of turbidity, by measuring absorbance at a specific wavelength, by size exclusion chromatography (in which aggregates of a protein will elute in different fractions compared to the protein in its native active state), HPLC, or other chromatographic methods. Other methods of measuring conformational change can be used, including using differential scanning calorimetry (DSC), e.g. to determine the temperature of denaturation, or circular dichroism (CD), which measures the molar ellipticity of the protein. Fluorescence can also be used to analyze the composition. Fluorescence encompasses the release or absorption of energy in the form of light or heat, and changes in the polar properties of light. Fluorescence emission can be intrinsic to a protein or can be due to a fluorescence reporter molecule, that for example binds to the hydrophobic pockets of partially unfolded proteins. An increase in binding of reporter molecules can be monitored by detection of the fluorescence signal of a protein sample. Other means for measuring stability can be used and are well known to persons of skill in the art.

In experiments carried out, first, the viscosity lowering potential of meglumine, ornithine, carnitine, benzenesulfonic acid and sodium p-toluene sulfonic acid, gluconic acid, glucuronic acid, aminocaproic acid and succinate alone are tested in combination with six types of antibodies (mAbA, mAbB mAbC (IgG2), mAbD, mAbE, mAbF) and one fusion protein (FusionA). The concentrations of the proteins are adjusted either at 98 mg/ml or 99 mg/ml or 173 mg/ml or 177 mg/ml or 200 mg/ml or 220 mg/ml or 260 mg/ml or 270 mg/ml to create high viscosity levels.

As already described above, the pH value of these formulations is of particular importance for their effectiveness and the usability of the respective pharmaceutically active protein. It is therefore desirable that the pH of the protein formulations investigated is adjusted in the range of between about 4.5 to about 8.0. Depending on the nature of the containing protein or peptide the pH value is adjusted preferably in a range between about 4.6 to about 5.4 or in a range between about 5.4 to about 7.9. The buffers used to adjust the pH are preferably an acetate buffer (25 mM) at pH 5 and phosphate buffered saline (10 mM) at pH 7. If necessary, however, another buffer can be used, which is compatible with the contained pharmaceutically active protein and physiologically acceptable.

The concentrations of the viscosity lowering agents are adjusted in a range from between 50 mM towards 500 mM (Examples 1 A-E). A chip-based (micro-electro-mechanical system) capillary rheometer, m-VROC™ (RheoSence, San Ramon, CA), was employed to measure the dynamic viscosity. In general, the dynamic viscosity which is also referred to as absolute viscosity (coefficient of absolute viscosity) is a measure of internal resistance which can be determined by the self-association of the protein molecules within a highly concentrated solution.

Determined viscosities clearly indicate, that applying solely meglumine, ornithine, carnitine, benzenesulfonic acid and sodium p-toluene sulfonic acid, gluconic acid, glucuronic acid, aminocaproic acid and succinate at a certain concentration together with a specific antibody or fusion protein results in a measurable significant reduction of viscosity of highly concentrated protein solutions.

However, particularly unexpectedly the experiments have shown, that the combined addition of meglumine, ornithine or carnitine and of a counterion selected from toluene sulfonate, benzenesulfonic acid, gluconic acid, glucuronic acid, aminocaproic acid and succinate leads to a significantly higher viscosity reduction.

As already pointed out, especially if mixtures of meglumine or of ornithine together with one of the counterions selected from toluene sulfonate and benzenesulfonic acid, gluconic acid, glucuronic acid, aminocaproic acid and succinate are added in equimolar amounts to the concentrated protein solution, for example to solutions of (mAbA and mAbB), a particularly good viscosity reduction is achieved.

In further experiments, the potential of mixtures of either the cationic amino sugar meglumine or the amino acid ornithine or of carnitine in combination with sodium p-toluene sulfonate, benzenesulfonic acid, gluconic acid, glucuronic acid, aminocaproic acid or succinate as a negative counterion to reduce the viscosity of highly concentrated antibody solutions (mAbA & mAbB) was investigated.

In further experiments, the potential of mixtures of either the cationic amino sugar meglumine or the amino acid ornithine in combination with sodium p-toluene sulfonate or benzenesulfonic acid as a negative charged counterion to reduce the viscosity of highly concentrated antibody solutions (mAbA & mAbB) was investigated. For each of these studies, mixtures of equimolar amounts of these excipients were added. Particularly good results were found here for concentrations of 150 mM (Examples 2 A-C).

All model antibodies were formulated at a rather high concentrations of about 100 mg/ml, some of about 150 mg/ml, especially of more than 200 mg/ml, and in particular of 220 mg/ml (mAbB) and 270 mg/mL (mAbA) in 10 mM phosphate buffer saline at pH 7. A chip-based (micro-electro-mechanical system) capillary rheometer, m-VROC™ (RheoSence, San Ramon, CA), was employed to measure the viscosity.

In all cases, the specific equimolar mixtures at a concentration of 150 mM of the cationic amino-sugar meglumine or the amino acid ornithine and a negatively charged counter ion like sodium-p-toluene sulfonate or benzenesulfonic acid show a significant reduction of the viscosity measured in the highly concentrated antibody solutions.

The viscosity lowering potential of meglumine and L-ornithine hydrochloride is tested in concentrated solutions comprising three different types of antibodies (chimeric IgG1, human IgG2, humanized IgG4). The average concentrations of these solutions were 99 mg/ml, 173 mg/ml or 177 mg/ml.

In experiments, it has been found that both excipients can significantly reduce the viscosity of antibody formulations when added to the protein solution at a concentration of 150 mM, respectively.

Also in solutions in which mAbD is contained as a protein, the addition of each 150 mM sodium p-toluenesulfonate and benzenesulfonic acid causes a significant reduction in viscosity.

Furthermore, the addition of 150 mM D-gluconic acid sodium salt to an mAbD-containing solution leads to a lowering of the viscosity.

The use of an equimolar combination of L-ornithine hydrochloride or meglumine with sodium p-toluene sulfonate or benzene sulfonic acid also decreased the viscosity of highly concentrated antibody solutions (mAbD & mAbE) markedly. In addition, as shown by the experiments carried out, various other combinations of the auxiliaries mentioned herein reduce the viscosity of high concentration antibody solutions.

Therefore, the combinations of excipients mentioned here are not exhaustive, and there are other possible combinations that lead to corresponding results.

The experiments have also shown a further advantageous effect, which results from the addition of the excipients mentioned here. Since usually used in pharmaceutics formulations for reliable effect even after several weeks storage time still have to have their activity, appropriate storage experiments were carried out and then checked the stability of the proteins.

For example, the stability of mAbD, indicated by the amount of monomer, can be improved during an accelerated stability study by the addition of 150 mM meglumine, 150 mM L-ornithine hydrochloride or an equimolar combination of L-ornithine hydrochloride and sodium-p-toluene-sulfonate, each 75 mM.

In this regard, the attempts to reduce the viscosity of the various protein solutions have shown that, depending on the protein contained in the particular solution, different additives result in the best stabilizations and reductions in viscosities.

In this context the best formulation for the protein mAbD is a composition comprising 5 mM phosphate buffer, 146 mM sucrose, 0.05 g/L Polysorbat 80, 75 mM L-ornitine hydrochloride, and 75 mM Sodium-p-toluenesulfonate dissolved in Milli-Q-Water and adjusted to pH 7.2.

For MAbE in turn the best formulation is a composition comprising 20 mM Acetate buffer, 0.1 g/L Polysorbate 80, 150 mM Meglumine dissolved in Milli-Q-Water and adjusted to pH 5.0, and for MAbF the best formulation is a composition comprising 20 mM acetate buffer, 205 mM sucrose, 75 mM meglumine, 75 mM D-gluconic acid sodium salt dissolved in Milli-Q-Water and adjusted to pH 5.5.

Preferred Embodiments:

Particularly preferred embodiments of the present invention consist in adding excipients selected from the group consisting of meglumine, ornithine, sodium-p-toluene sulfonate, benzenesulfonic acid, gluconic acid, glucoronic acid, aminocaproic acid, carnitine, and succinate, either alone or in combination, to highly concentrated protein solutions as described above for viscosity reduction. Particularly preferably, the addition of meglumine either in combination with benzenesulfonic acid or with sodium p-toluene sulfonic acid as counterion leads to good viscosity reductions. In another preferred embodiment of the present invention ornithine in combination with benzenesulfonic acid or with sodium p-toluene sulfonic acid as counterion leads also to good viscosity reductions. Accordingly, viscosity reduction in concentrated protein solutions by Meg>Meg-sodium-p-toluene sulfonate>sodium-p-toluene sulfonate>benzenesulfonic acid>ornithine>all other combinations of these excipient are preferred.

The formulation of solution preparations and freeze drying can be carried out by the methods as described above and as disclosed in the following examples.

The present description enables one of ordinary skill in the art to practice the present invention comprehensively. Even without further comments, it is therefore assumed that a person of ordinary skill in the art will be able to utilise the above description in the broadest scope.

Although the invention has been described in connection with preferred embodiments, it should be understood that various modifications, additions and alterations may be made to the invention by one skilled in the art without departing from the spirit and scope of the invention as defined in the appended claims.

If anything is unclear, it is understood that the publications and patent literature cited and known to the artisan should be consulted. Accordingly, cited documents are regarded as part of the disclosure content of the present description and are incorporated herein by reference.

For better understanding and in order to illustrate the invention, examples are presented below which are within the scope of protection of the present invention. These examples also serve to illustrate possible variants.

Furthermore, it goes without saying to one of ordinary skill in the art that, both in the examples given and also in the remainder of the description, the component amounts present in the compositions always only add up to 100% by weight or mol %, based on the composition as a whole, and cannot exceed this percentage, even if higher values could arise from the percent ranges indicated. Unless indicated otherwise, % data are therefore % by weight or mol %, with the exception of ratios, which are shown in volume data.

EXAMPLES

Example 1

Viscosity reducing effect of meglumine, L-ornithine hydrochloride, sodium-p-toluene sulfonate and benzenesulfonic acid in highly concentrated protein solutions Example 1A) Viscosity of mAbA at a protein concentration of 260 mg/ml is significantly reduced by meglumine, L-ornithine hydrochloride and sodium-p-toluene sulfonate, but not by benzenesulfonic acid at 50 mM.

Example 1B) Due to the environmental change of buffer and pH, viscosity of mAbA is also significantly reduced by benzene-sulfonic-acid as excipient (at 150 mM).

Example 1C) Viscosity of mAbB at a protein concentration of 200 mg/ml shows a significantly reduced viscosity by meglumine, L-ornithine hydrochloride and sodium-p-toluene sulfonate at 500 mM.

Example 1D) for mAbC the excipient benzene-sulfonic-acid exhibits a clear viscosity reducing effect at 150 mM. For the other investigated excipients, a reducing effect was found, too.

Example 1E) for the fusion protein 'FusionA' only a slightly viscosity reducing effect was found for all excipients. Only benzene-sulfonic-acid at a concentration of 50 mM shows a stronger reduction.

Example 1 A)

Viscosity reducing effect of meglumine, L-ornithine hydrochloride and sodium-p-toluene sulfonate in highly concentrated mAbA solution (260 mg/ml) formulated in a 25 mM Acetate buffer pH 5.0 shown in FIG. 1.

Buffer Preparation:
 25 mM Sodium Acetate Trihydrate and 25 mM Glacial Acid were dissolved in Milli-Q-Water and the pH was adjusted to 5.0 (±0.1) using HCl or NaOH, if necessary.

Sample Preparation:
 Excipient solutions of 50 mM of meglumine, L-ornithine hydrochloride, sodium-p-toluene sulfonate and benzenesulfonic acid were prepared in 25 mM Acetate buffer pH 5.0. The pH was adjusted using HCl or NaOH, if necessary.
 A concentrated mAbA solution containing the relevant excipient was prepared with ultra-centrifugal filters (30 kDa MWCO) by exchanging the buffer with the relevant excipient solution above and concentrating the protein by reducing the volume of the solution. Afterwards the concentrated protein solution was diluted to 260 mg/ml using the appropriate excipient solution above.

Viscosity Measurements:
 The m-VROC™ Technology (RheoSense, San Ramon, California, USA) was used for viscosity measurements. Measurements were performed using a 500 µl syringe and a shear rate of 5000 s$^{-1}$. The required sample volume was 200 µl and samples were tested in triplicate.

Example 1 B)

Figure 2:
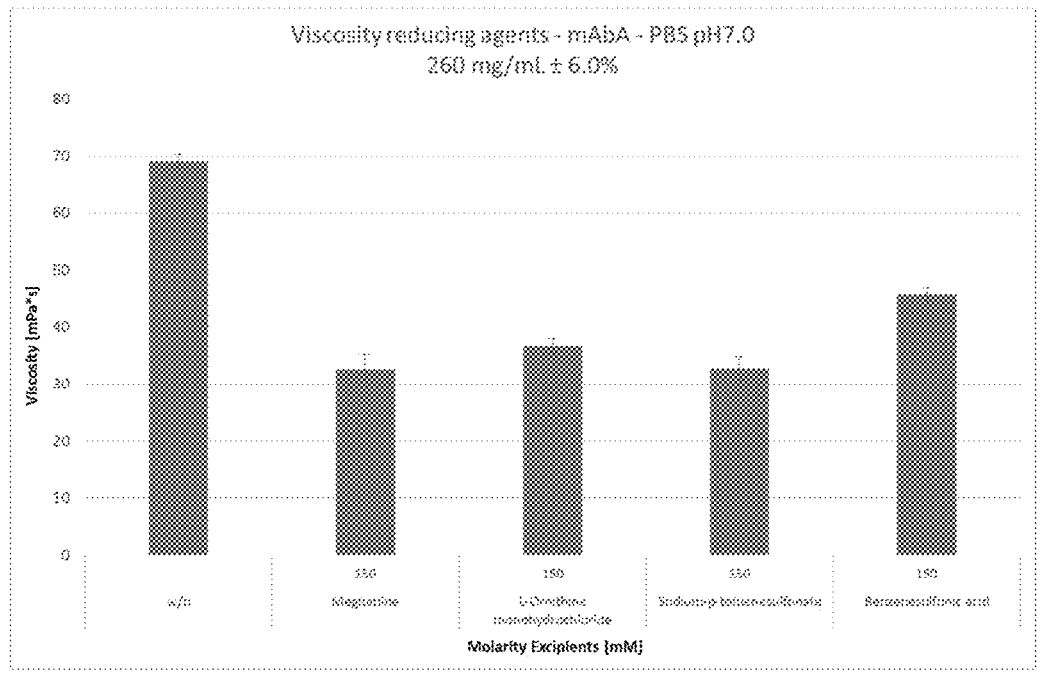

Viscosity reducing effect of meglumine, L-ornithine hydrochloride, sodium-p-toluene sulfonate and benzenesulfonic acid in a highly concentrated mAbA solution (260 mg/mL) formulated in Phosphate Buffered Saline (PBS) pH 7.0 shown in FIG. 2.

Buffer Preparation:
The buffer contained 0.01 M Phosphate Buffer, 0.0027 M Potassium Chloride and 0.137 M Sodium Chloride dissolved in Milli-Q-Water. The pH was adjusted to 7.0 (±0.1) using HCl or NaOH, if necessary.

Sample Preparation:
Excipient solutions of 150 mM of meglumine, L-ornithine hydrochloride, sodium-p-toluene sulfonate and benzenesulfonic acid were prepared in PBS pH 7.0. The pH was adjusted using HCl or NaOH, if necessary.

A concentrated mAbA solution containing the relevant excipient was prepared with ultra-centrifugal filters (30 kDa MWCO) by exchanging the buffer with the relevant excipient solution above and concentrating the protein by reducing the volume of the solution. Afterwards the concentrated protein solution was diluted to 260 mg/mL using the appropriate excipient solution above.

The viscosity measurement was performed as described in Example 1 A).

Figure 3:
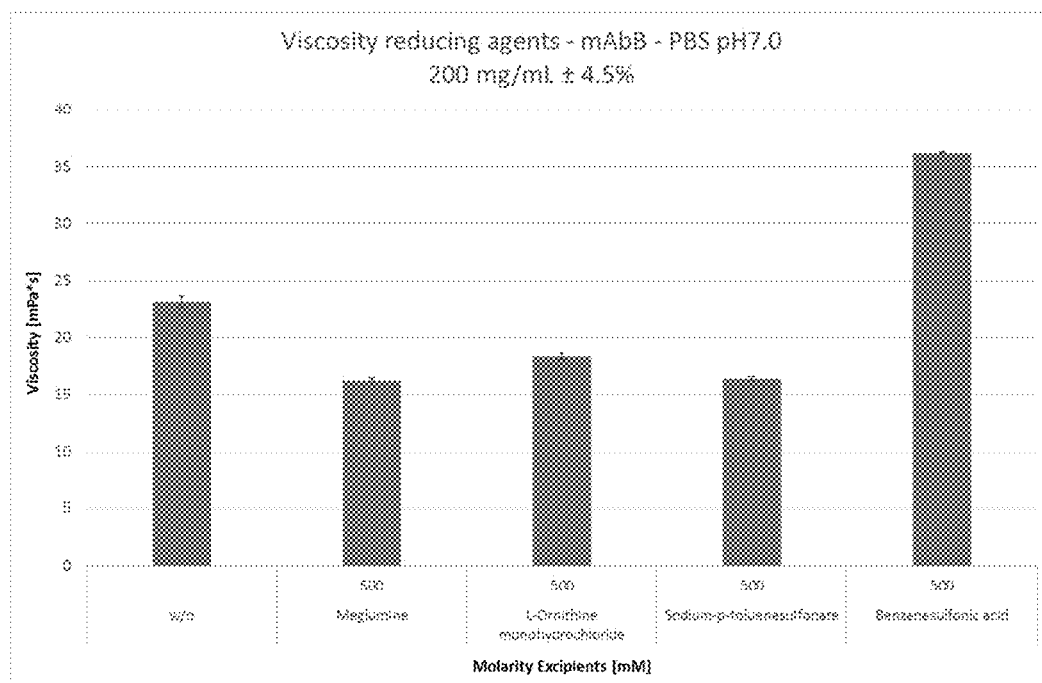

Example 1 C)

viscosity reducing effect of meglumine, L-ornithine hydrochloride and sodium-p-toluene sulfonate in a highly concentrated mAbB solution (200 mg/mL) formulated in PBS pH 7.0 shown in FIG. 3.

Buffer Preparation:
The buffer preparation was performed as described in Example 1 B).

Sample Preparation:
Excipient solutions of 500 mM of meglumine, L-ornithine hydrochloride, sodium-p-toluene sulfonate and benzenesulfonic acid were prepared in PBS pH 7.0. The pH was adjusted using HCl or NaOH, if necessary.

A concentrated mAbB solution containing the relevant excipient was prepared with ultra-centrifugal filters (30 kDa MWCO) by exchanging the buffer with the relevant excipient solution above and concentrating the protein by reducing the volume of the solution. Afterwards the concentrated protein solution was diluted to 200 mg/mL using the appropriate excipient solution above.

The viscosity measurement was performed as described in Example 1 A).

Example 1 D)

Figure 4:
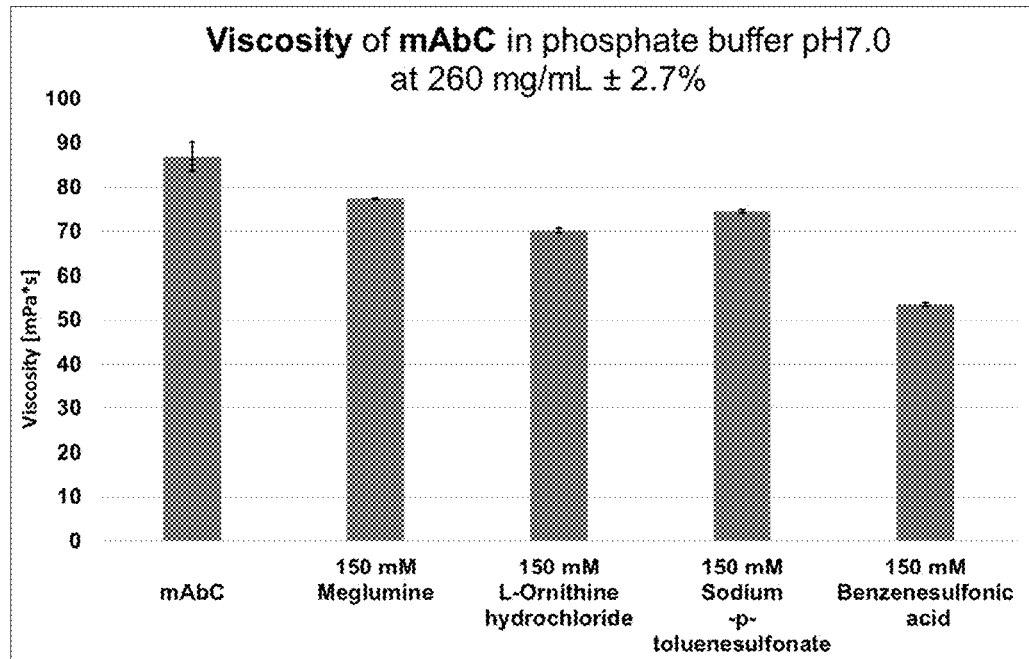

Viscosity reducing effect of meglumine, L-ornithine, sodium-p-toluene sulfonate and benzenesulfonic acid for mAbC formulated at 260 mg/mL (+/−2.7%) in phosphate buffer pH 7 shown in FIG. 4.

Buffer Preparation:
A phosphate buffer was prepared containing 100 mM sodium phosphate, 2.7 mM potassium chloride and 137 mM sodium chloride.

Sample Preparation:
Excipient solutions of 150 mM meglumine, L-ornithine, sodium-p-toluene sulfonate and benzenesulfonic acid were prepared in the phosphate buffer. The pH value was checked and adjusted to 7.0 (+/−0.1) using hydrochloric acid or sodium hydroxide, if necessary.

A protein solution of mAbC (app. 147 kDa) at 71 mg/ml was washed and concentrated in phosphate buffer pH 7 containing 150 mM of the corresponding excipient.

Washing and concentration of mAbC to 260 mg/ml was done using ultra centrifugal filter units with a 30 kDa MWCO.

The mVROC method was performed as described in Example 1 A).

Example 1 E)

Figure 5:
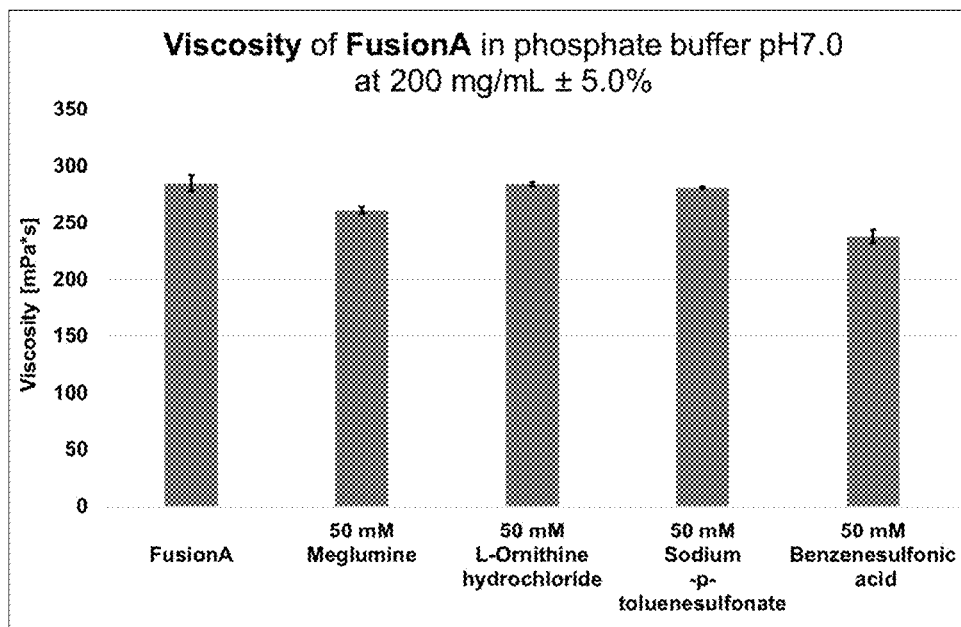

Viscosity reducing effect of meglumine, L-ornithine hydrochloride, sodium-p-toluene sulfonate and benzenesulfonic acid for fusionA formulated at 200 mg/ml (+/−5.0%) in phosphate buffer pH 7 shown in FIG. 5.

Buffer Preparation:
A phosphate buffer was prepared containing 100 mM sodium phosphate, 2.7 mM potassium chloride and 137 mM sodium chloride.

Sample Preparation:
Excipient solutions of 50 mM meglumine, L-ornithine hydrochloride, sodium-p-toluene sulfonate and benzenesulfonic acid were prepared in the phosphate buffer. The pH value was checked and adjusted to 7.0 (+/−0.1) using hydrochloric acid or sodium hydroxide, if necessary.

A protein solution of FusionA (app. 51 kDa) at 50 mg/ml was washed and concentrated in phosphate buffer pH 7 containing 300 mM of the corresponding excipient.

Washing and concentration of mAbD to 200 mg/ml was done using ultra centrifugal filter units with a 30 kDa MWCO at 2,000×g.

The mVROC method was performed as described in Example 1 A).

Example 2

Viscosity reducing effect of combination of two excipients (meglumine, L-ornithine hydrochloride, sodium-p-toluene sulfonate and benzenesulfonic acid) in highly concentrated protein solutions Example 2 A) shows a viscosity reduction of mAbA at a concentration of 270 mg/ml (+/−2.6%) using combinations of meglumine and benzenesulfonic acid or meglumine and sodium-p-toluene sulfonate (each present at 75 mM in the PBS pH 7).

Example 2 B) exhibits a stronger viscosity reducing effect on mAbA using the excipient combination of L-ornithine hydrochloride with benzenesulfonic acid (both present at 75 mM in the buffer). The combination of L-ornithine hydrochloride and sodium-p-toluene sulfonate has a reducing effect, too.

Example 2 C) shows a clear reduction of the viscosity of mAbB at a concentration of 220 mg/ml in a PBS buffer at pH 7 for all combinations of excipients investigated. The highest influence was caused by the combination of meglumine and sodium-p-toluene sulfonate (both 75 mM) reducing the viscosity of the pure mAbB in PBS from 125 mPa*s to 37.7 mPa*s.

Example 2 A)

Figure 6:
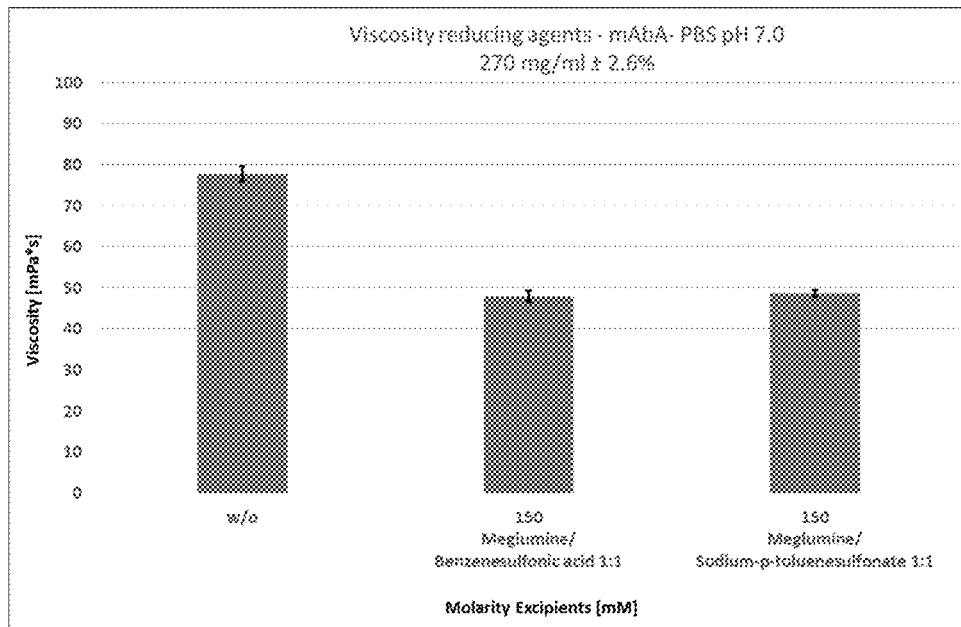

Viscosity reducing effect of the combination of the excipients Meglumine and benzenesulfonic acid (1:1), Meglumine and sodium-p-toluene sulfonate (1:1) at a cumulative concentration of 150 mM in a highly concentrated mAbA solution (270 mg/ml) formulated in PBS pH 7.0 shown in FIG. 6.

Buffer Preparation:
The buffer preparation was performed as described in Example 1 B).

Sample Preparation:
Excipient solutions containing 75 mM meglumine and 75 mM benzenesulfonic acid or 75 mM sodium-p-toluene sulfonate were prepared in PBS pH 7.0. The pH was adjusted using hydrochloric acid or sodium hydroxide, if necessary.

A concentrated mAbA solution containing the relevant excipient combination was prepared with ultra-centrifugal filters (30 kDa MWCO) by exchanging the buffer with the relevant excipient combination solution above and concentrating the protein by reducing the volume of the solution. Afterwards the concentrated protein solution was diluted to 270 mg/ml using the appropriate excipient combination solution above.

The viscosity measurement was performed as described in Example 1 A).

Example 2 B)

Figure 7:
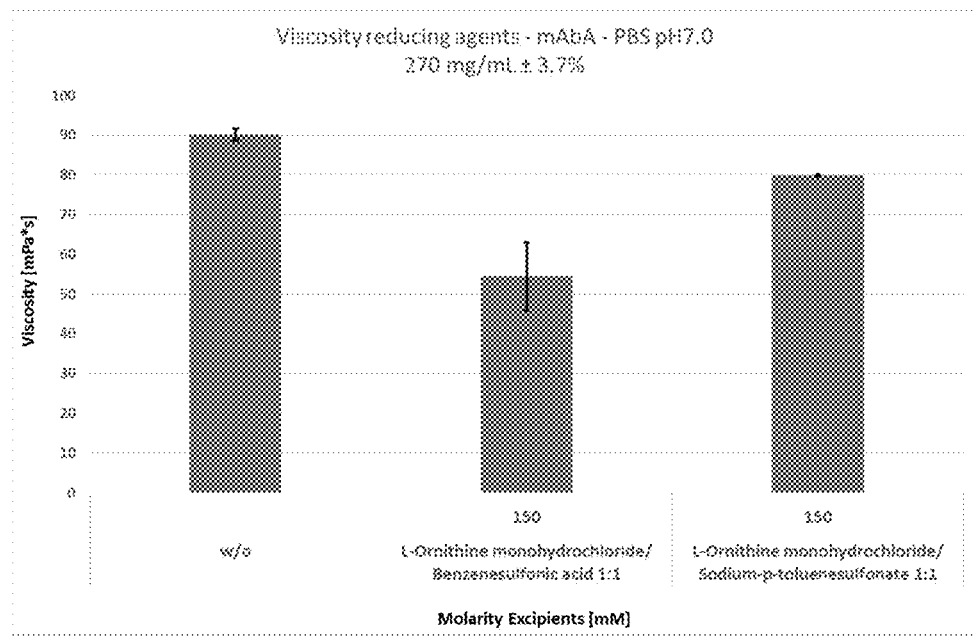

Viscosity reducing effect of the combination of the excipients L-ornithine hydrochloride and benzenesulfonic acid (1:1), L-ornithine hydrochloride and sodium-p-toluene sulfonate (1:1) at a cumulative concentration of 150 mM in a highly concentrated mAbA solution (270 mg/ml) formulated in PBS pH 7.0 shown in FIG. 7.

Buffer Preparation:
The buffer preparation was performed as described in Example 1 B).

Sample Preparation:
Excipient solutions containing 75 mM L-ornithine hydrochloride and 75 mM benzenesulfonic acid or 75 mM sodium-p-toluene sulfonate were prepared in PBS pH 7.0. The pH was adjusted using hydrochloric acid or sodium hydroxide, if necessary.

The remaining sample preparation was performed as described in Example 2 A).

The viscosity measurement was performed as described in Example 1 A).

Example 2 C)

Figure 8:
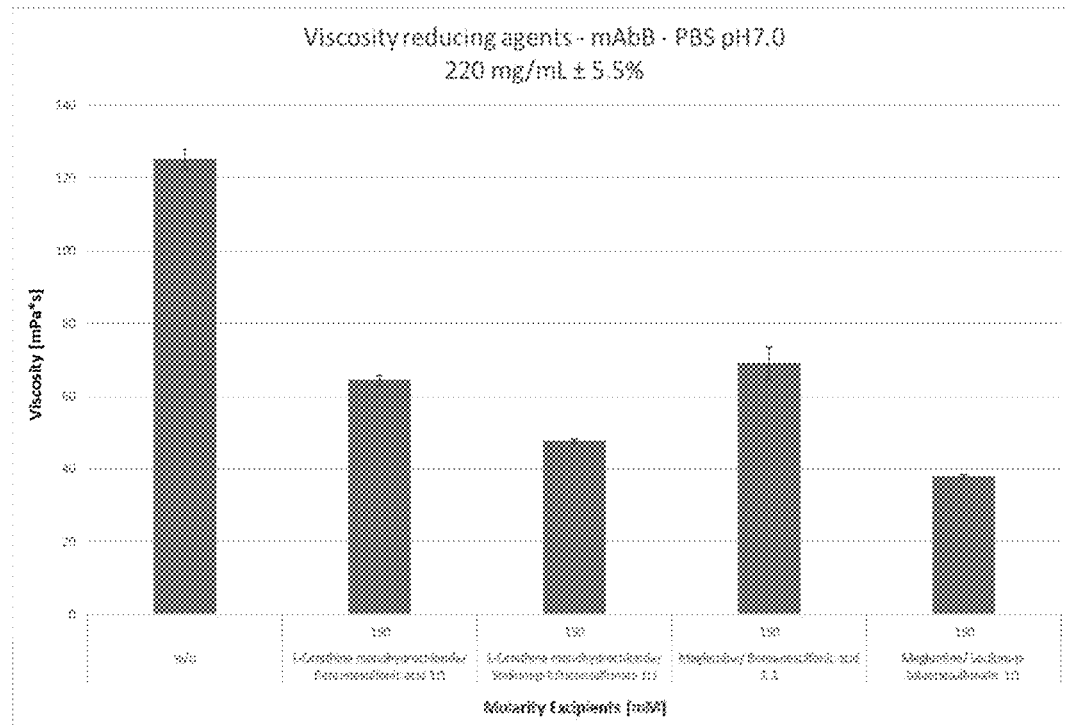
Figure 9:
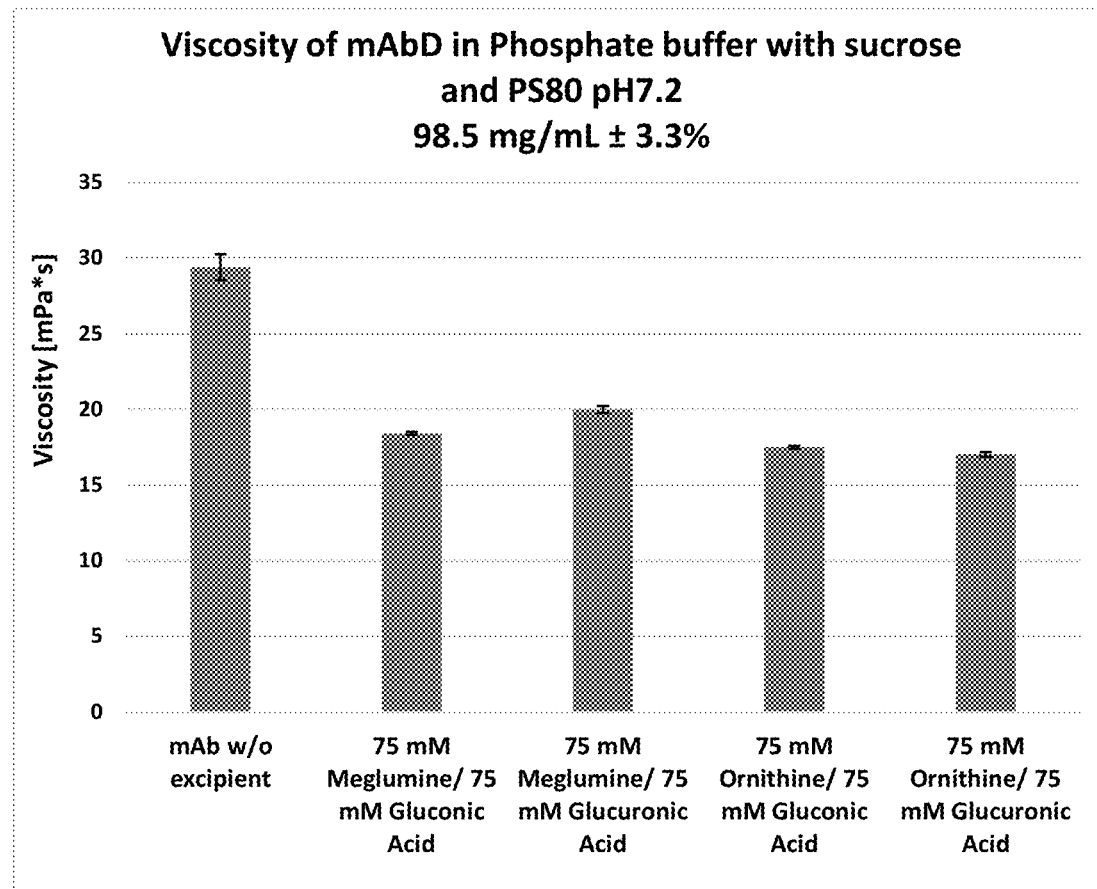
Figure 10:
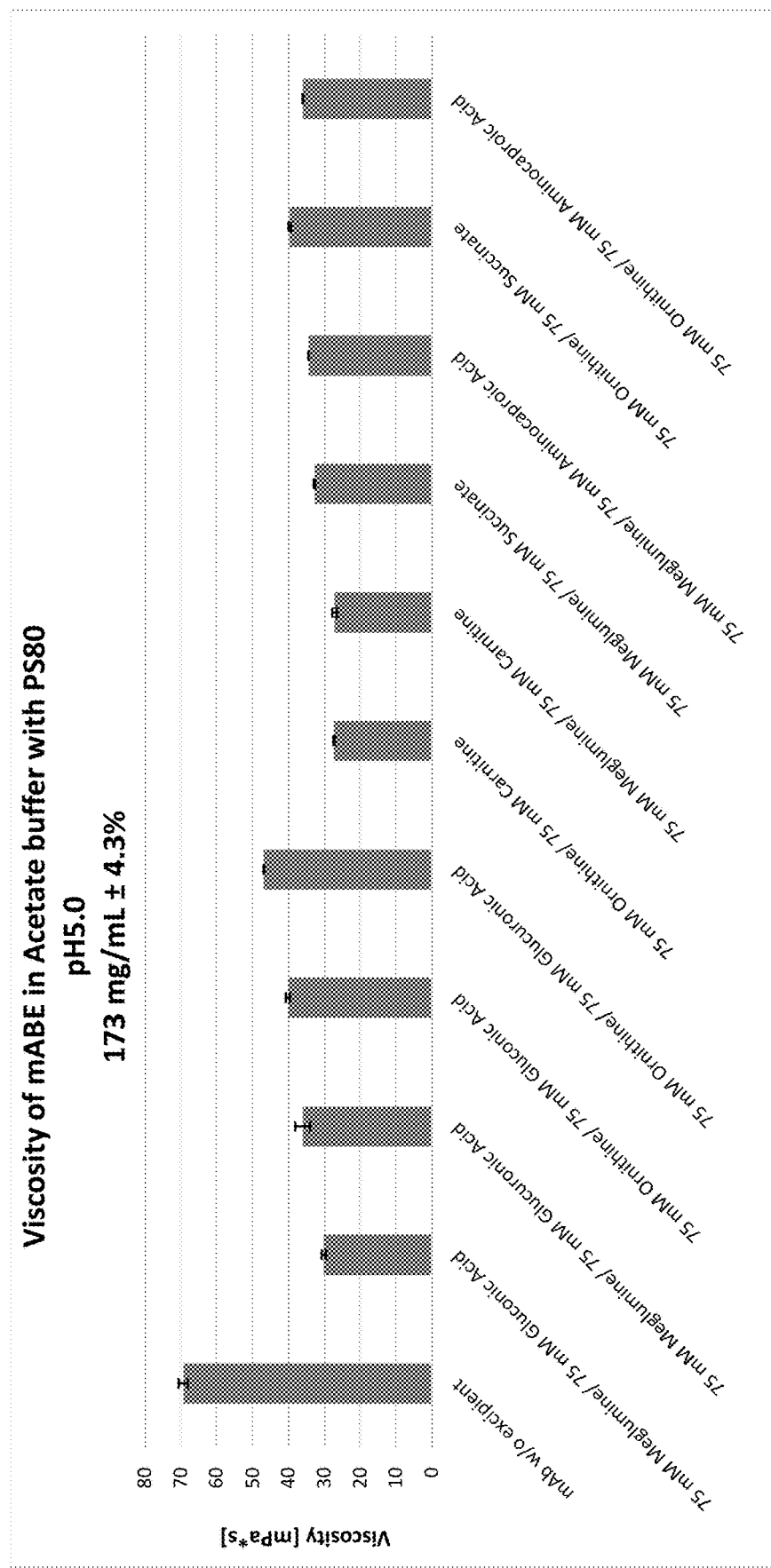

Viscosity reducing effect of the combination of the excipients L-ornithine hydrochloride and benzenesulfonic acid (1:1), L-ornithine hydrochloride and sodium-p-toluene sulfonate (1:1), meglumine and benzenesulfonic acid (1:1), meglumine and sodium-p-toluene sulfonate (1:1) in a highly concentrated mAbB solution (220 mg/mL) formulated in PBS pH 7.0 shown in FIG. 8 to 10.

Buffer Preparation:
The buffer preparation was performed as described in Example 1 B).

Sample Preparation:
Excipient solutions of 75 mM L-ornithine hydrochloride and 75 mM benzenesulfonic acid, 75 mM L-ornithine hydrochloride and 75 mM sodium-p-toluene sulfonate, 75 mM meglumine and 75 mM benzenesulfonic acid, 75 mM meglumine and 75 mM sodium-p-toluene sulfonate were prepared in PBS pH 7.0. The pH was adjusted using hydrochloric acid or sodium hydroxide, if necessary.

A concentrated mAbB solution containing the relevant excipient combination was prepared with ultra-centrifugal filters (30 kDa MWCO) by exchanging the buffer with the relevant excipient combination solution above and concentrating the protein by reducing the volume of the solution. Afterwards the concentrated protein solution was diluted to 220 mg/mL using the appropriate excipient combination solution above.

The viscosity measurement was performed as described in Example 1 A).

Example 3

Buffer Preparation:
The buffer contains 5 mM phosphate buffer, 146 mM sucrose, 0.05 g/L Polysorbat 80 dissolved in Milli-Q-Water. The pH is adjusted to pH 7.2 (±0.05) using HCl or NaOH, if necessary.

Sample Preparation:
The excipient solutions are prepared with a concentration of 150 mM in the phosphate buffer mentioned above.

The combinations of two excipients are prepared with an equimolar concentration of 75 mM for each excipient in the phosphate buffer.

A concentrated MAbD solution is prepared using an ultra-centrifugal filter (30 kDa MWCO) by buffer exchange with the respective excipient solution. The concentrated protein solution is diluted to 100 mg/mL with the corresponding excipient solution above.

The viscosity measurement is performed as described in Example 1 A).

Example 4

Buffer Preparation:
The buffer solution containing 20 mM acetate buffer, 0.1 g/L Polysorbat 80 is prepared by dissolving in Milli-Q-Water. The pH is adjusted to pH 5.0 (±0.05) using HCl or NaOH, if necessary.

Sample Preparation:
The excipient solutions are prepared with a concentration of 150 mM in the acetate buffer as mentioned above.

The combinations of two excipients are prepared with an equimolar concentration of 75 mM of each excipient in said acetate buffer.

A concentrated MAbE solution is prepared using an ultra-centrifugal filter (30 kDa MWCO) by buffer exchange with the respective excipient solution. The concentrated protein solution is diluted to a concentration of 170 mg/mL with the corresponding excipient solution mentioned above.

The viscosity measurement is performed as described in Example 1 A).

Example 5

Buffer Preparation:
The buffer contained 20 mM acetate buffer, 205 mM sucrose dissolved in Milli-Q-Water. The pH was adjusted to pH 5.5 (±0.05) using HCl or NaOH, if necessary.

Sample Preparation:
The excipient solutions are prepared with a concentration of 150 mM in the Acetate buffer mentioned above.

The combinations of two excipients were prepared with an equimolar concentration of 75 mM for each excipient in the acetate buffer.

A concentrated MAbF solution is prepared using an ultra-centrifugal filter (30 kDa MWCO) by buffer exchange with the respective excipient solution. The concentrated protein solution is diluted to 180 mg/mL with the corresponding excipient solution above.

The viscosity measurement is performed as described in Example 1 A).

LIST OF FIGURES

FIG. 1 Example 1 A) Viscosity reducing effect of meglumine, L-ornithine hydrochloride and sodium-p-toluene sulfonate in highly concentrated mAbA solution (260 mg/ml) formulated in a 25 mM Acetate buffer pH 5.0

FIG. 2 Example 1 B) Viscosity reducing effect of meglumine, L-ornithine hydrochloride, sodium-p-toluene sulfonate and benzenesulfonic acid in a highly concentrated mAbA solution (260 mg/mL) formulated in Phosphate Buffered Saline (PBS) pH 7.0

FIG. 3 Example 1 C) viscosity reducing effect of meglumine, L-ornithine hydrochloride and sodium-p-toluene sulfonate in a highly concentrated mAbB solution (200 mg/mL) formulated in PBS pH 7.0

FIG. 4 Example 1 D) Viscosity reducing effect of meglumine, L-ornithine, sodium-p-toluene sulfonate and benzenesulfonic acid for mAbC formulated at 260 mg/mL (+/− 2.7%) in phosphate buffer pH 7

FIG. 5 Example 1 E) Viscosity reducing effect of meglumine, L-ornithine hydrochloride, sodium-p-toluene sulfonate and benzenesulfonic acid for fusionA formulated at 200 mg/ml (+/−5.0%) in phosphate buffer pH 7

FIG. 6 Example 2 A) Viscosity reducing effect of the combination of the excipients Meglumine and benzenesulfonic acid (1:1), Meglumine and sodium-p-toluene sulfonate (1:1) at a cumulative concentration of 150 mM in a highly concentrated mAbA solution (270 mg/ml) formulated in PBS pH 7.0

FIG. 7 Example 2 B) Viscosity reducing effect of the combination of the excipients L-ornithine hydrochloride and benzenesulfonic acid (1:1), L-ornithine hydrochloride and sodium-p-toluene sulfonate (1:1) at a cumulative concentration of 150 mM in a highly concentrated mAbA solution (270 mg/ml) formulated in PBS pH 7.0

FIG. 8 Example 2 C) Viscosity reducing effect of the combination of the excipients L-ornithine hydrochloride and benzenesulfonic acid (1:1), L-ornithine hydrochloride and sodium-p-toluene sulfonate (1:1), meglumine and benzenesulfonic acid (1:1), meglumine and sodium-p-toluene sulfonate (1:1) in a highly concentrated mAbB solution (220 mg/mL) formulated in PBS pH 7.0

FIG. 9: Example 3) Viscosity reducing effect of the combination of the excipients meglumine and gluconic acid (1:1), meglumine glucuronic acid (1:1), ornitine and gluconic acid (1:1), ornitine glucuronic acid (1:1), in a highly concentrated mAbD solution (100 mg/ml) formulated in a phosphate buffer pH 7.2

FIG. 10: Viscosity reducing effect of a concentrated protein solution of mAbE which is diluted to a concentration of 170 mg/mL with a solution comprising a combination of two excipients with an equimolar concentration of 75 mM for each excipient in an acetate buffer (pH 5.0) comprising Polysorbat 80 as described in Example 4.

Figure 11:
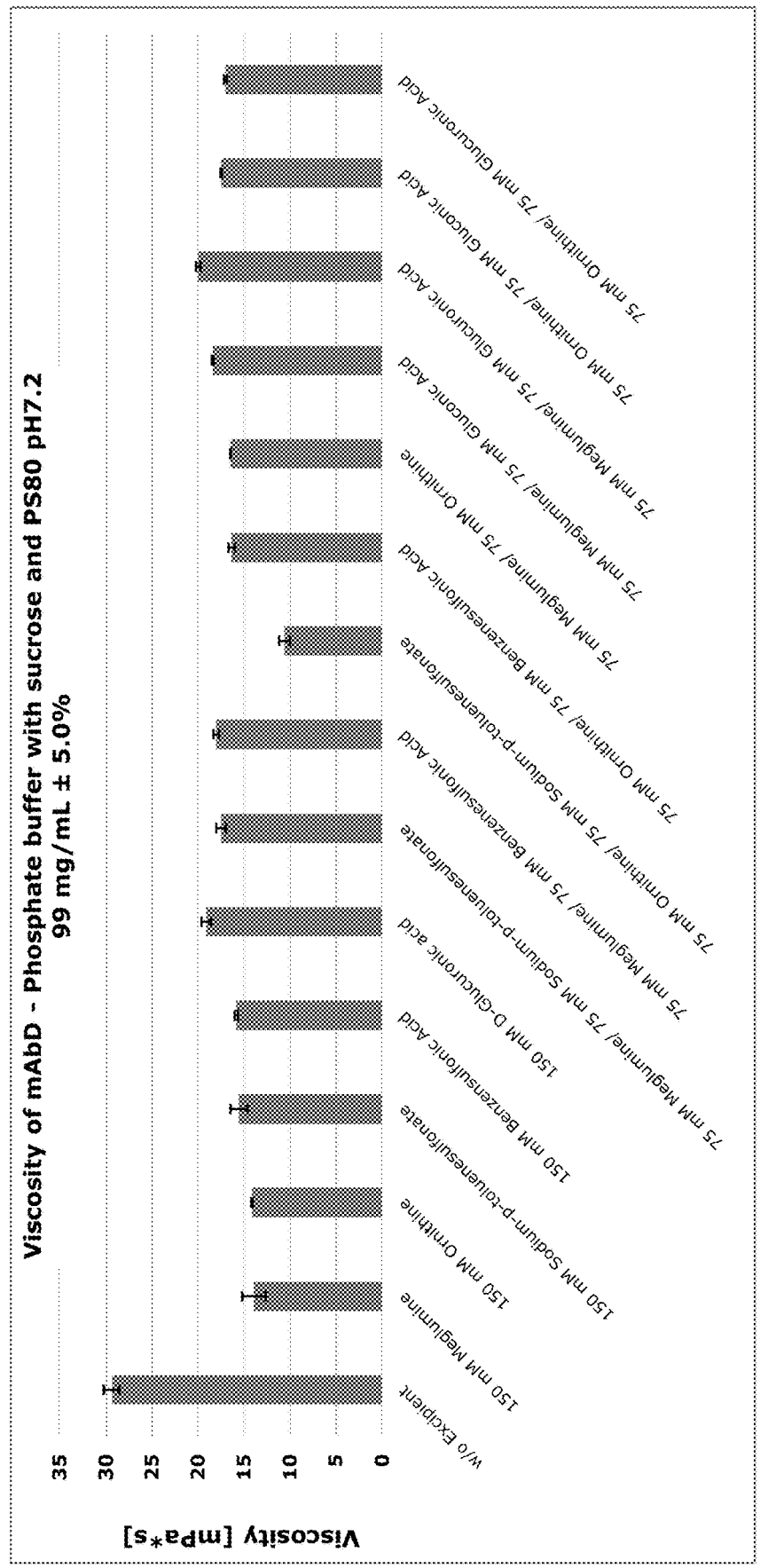

FIG. 11 Viscosity reducing effect of a concentrated protein solution of mAbD which is diluted to a concentration of 100 mg/mL with a solution comprising a combination of two excipients with an equimolar concentration of 75 mM for each excipient in the phosphate buffer (pH 7.2) comprising sucrose and Polysorbat 80 as described in Example 3

Figure 12:
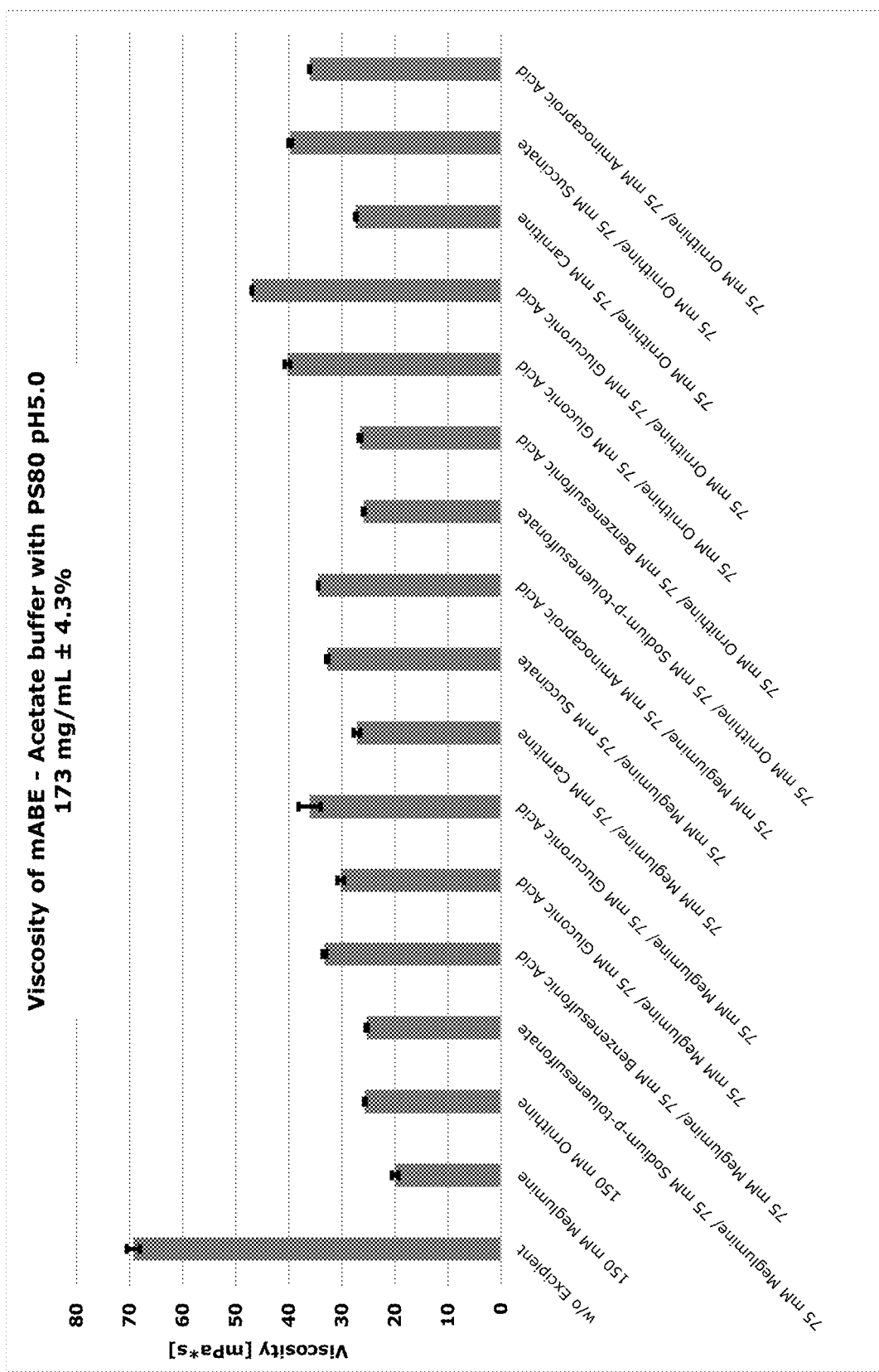

FIG. 12 Viscosity reducing effect of a concentrated protein solution of mAbE which is diluted to a concentration of 170 mg/mL with a solution comprising a combination of two excipients with an equimolar concentration of 75 mM for each excipient in an acetate buffer (pH 5.0) comprising Polysorbat 80 as described in Example 4.

Figure 13:
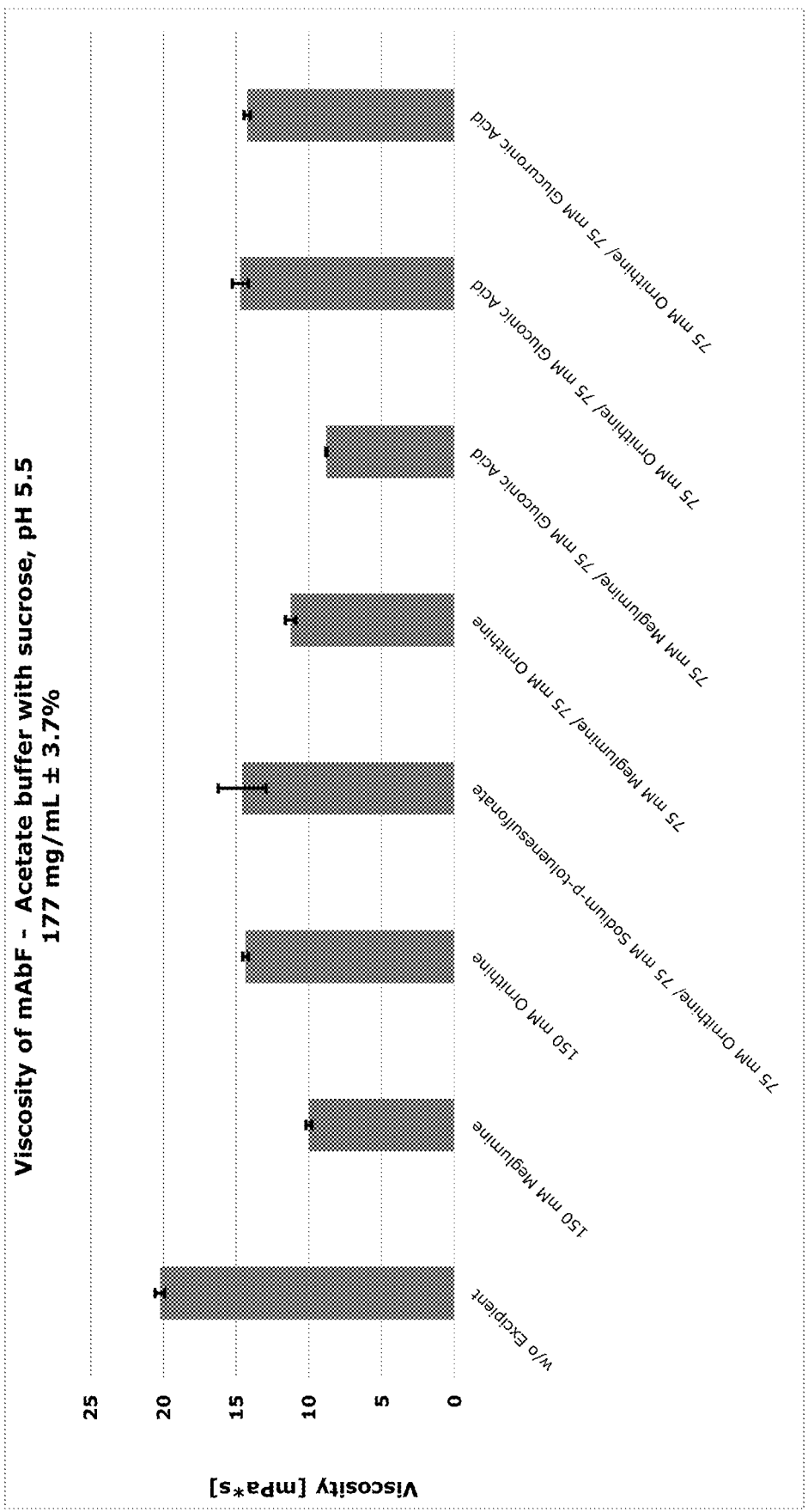

FIG. 13 Viscosity reducing effect of a concentrated protein solution of mAbF which is diluted to a concentration of about 180 mg/ml with a solution comprising a combination of two excipients with an equimolar concentration of 75 mM for each excipient in an acetate buffer solution (pH 5.5) comprising sucrose as described in Example 5.

Figure 14:
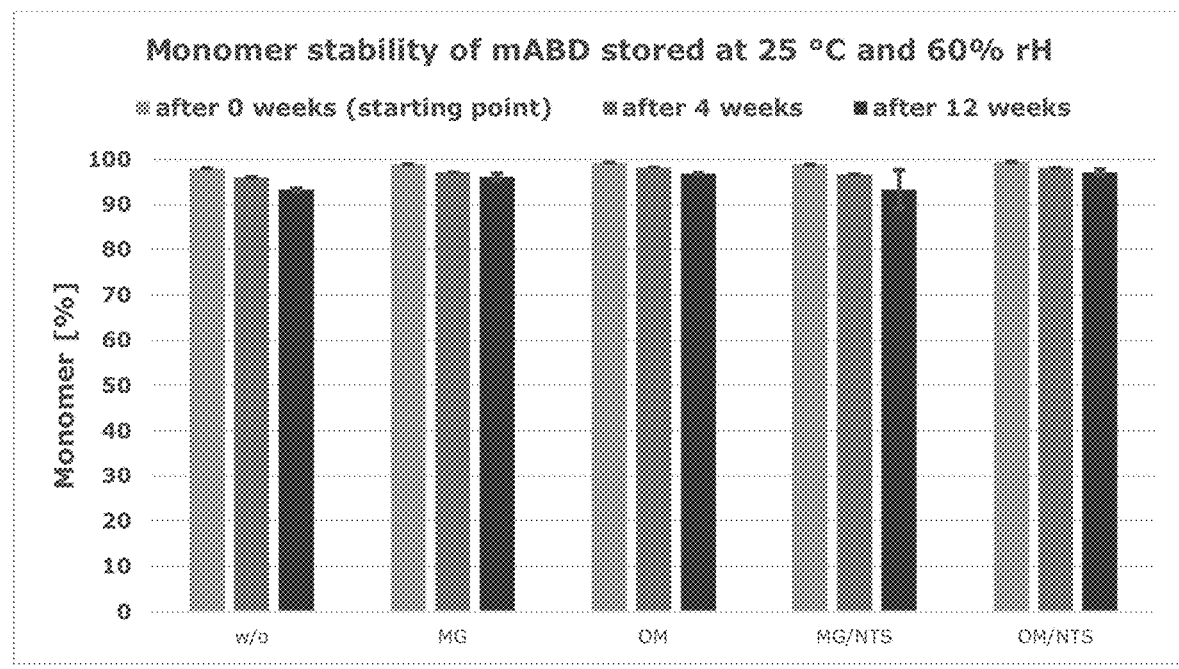

FIG. 14 Stability study for mAbD at 25° C. and 60% RH in the presence of various excipients over 12 weeks. (Abbreviations: MG=meglumine; OM=L-ornithine monohydrochloride; NTS=sodium-p-toluene sulfonate; w/o=without, this means market formulation without excipient).

What is claimed:

1. A method for reducing the viscosity of a liquid formulation comprising a pharmaceutically active protein in a concentration in the range of at least 50 mg/ml up to 300 mg/ml, the method comprising:
    combining the liquid formulation comprising protein with a viscosity-reducing concentration of one of the following combinations of excipients: meglumine+benzenesulfonic acid; ornithine+benzenesulfonic acid; ornithine+gluconic acid; ornithine+glucuronic acid, and mixtures of such combinations,
    wherein the amount of each of the excipients is from 50 to 300 mM.

2. The method of claim 1, wherein the pharmaceutically active protein is selected from antibodies, antibody fragments, minibodies, modified antibodies, antibody-like molecules, and fusion proteins.

3. The method of claim 1, wherein the combination of excipients is meglumine and benzenesulfonic acid.

4. The method of claim 1, wherein the combination of excipients is ornithine and benzenesulfonic acid.

5. The method of claim 1, wherein the combination of excipients is ornithine and gluconic acid.

6. The method of claim 1, wherein the combination of excipients is ornithine and glucuronic acid.

7. The method according to claim 3, wherein the meglumine and benzenesulfonic acid are added in equimolar amounts.

8. The method according to claim 1, wherein viscosity of the formulation is reduced by at least 12%.

9. The method according to claim 1, wherein viscosity of the formulation is reduced by at least 50%.

10. The method according to claim 1, wherein viscosity of the formulation is reduced by at least 25%.

11. The method according to claim 1, wherein the liquid formulation comprising protein and the combination of excipients has a pH in the range between about 4.5 to about 8.0.

12. The method according to claim 1, wherein the liquid formulation comprising protein and the combination of excipients has a pH in the range between about 5.4 to about 7.9.

13. The method according to claim 1, wherein the liquid formulation comprising protein and the combination of excipients has a pH of about 4.6 to about 5.4.

14. The method of claim 1, wherein the therapeutic protein is a monoclonal antibody.

15. The method of claim 1, wherein the therapeutic protein is a fusion protein.

16. The method of claim 1, wherein the liquid formulation contains the pharmaceutically active protein in a concentration in the range of at least 75 mg/ml up to 300 mg/ml.

17. The method of claim 1, wherein the liquid formulation contains the pharmaceutically active protein in a concentration in the range of at least 100 mg/ml up to 300 mg/ml.

* * * * *